United States Patent
Ying et al.

(10) Patent No.: US 10,449,541 B2
(45) Date of Patent: Oct. 22, 2019

(54) MICROFLUIDIC DEVICE

(71) Applicant: Agency for Science, Technology and Research, Singapore (SG)

(72) Inventors: Jackie Y. Ying, Singapore (SG); Saravana Kumar Kumarasamy, Singapore (SG); Rensheng Deng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 203 days.

(21) Appl. No.: 15/025,858

(22) PCT Filed: Sep. 30, 2013

(86) PCT No.: PCT/SG2013/000423
§ 371 (c)(1),
(2) Date: Mar. 29, 2016

(87) PCT Pub. No.: WO2015/047190
PCT Pub. Date: Apr. 2, 2015

(65) Prior Publication Data
US 2016/0243550 A1    Aug. 25, 2016

(51) Int. Cl.
*B01L 3/00* (2006.01)
*C12Q 1/689* (2018.01)
*C12Q 1/686* (2018.01)

(52) U.S. Cl.
CPC ... *B01L 3/502746* (2013.01); *B01L 3/502738* (2013.01); *C12Q 1/686* (2013.01);
(Continued)

(58) Field of Classification Search
None
See application file for complete search history.

(56) References Cited

U.S. PATENT DOCUMENTS 6,296,020 B1    10/2001  McNeely et al.
6,637,463 B1    10/2003  Lei et al.
(Continued)

FOREIGN PATENT DOCUMENTS

WO    WO-2013/132447 A1    9/2013

OTHER PUBLICATIONS

International Search Report for PCT/SB2013/000423, 5 pages (dated Dec. 2, 2013).
(Continued)

*Primary Examiner* — Xiaoyun R Xu
(74) *Attorney, Agent, or Firm* — Choate, Hall & Stewart, LLP

(57) ABSTRACT

There is provided a microfluidic device comprising: a plurality of wells, each well having an inlet and an outlet, wherein the inlets are in fluid communication with one or more entry channels and the outlets are in fluid communication with one or more exit channels, wherein said outlet is connected to the exit channel via an outlet connecting channel and said inlet is connected to the entry channel via an inlet connecting channel wherein the dimension of the outlet connecting channel is configured such that the surface tension of a liquid comprised in the well prevents the release of the liquid through the outlet connecting channel. There is also provided a system, method and use of the device.

19 Claims, 12 Drawing Sheets
Specification includes a Sequence Listing.

(52) U.S. Cl.
CPC ...... *C12Q 1/689* (2013.01); *B01L 2200/0642* (2013.01); *B01L 2200/0647* (2013.01); *B01L 2300/0636* (2013.01); *B01L 2300/0803* (2013.01); *B01L 2300/0864* (2013.01); *B01L 2300/0867* (2013.01); *B01L 2300/0893* (2013.01); *B01L 2300/18* (2013.01); *B01L 2400/0487* (2013.01); *B01L 2400/06* (2013.01); *B01L 2400/0677* (2013.01); *B01L 2400/0688* (2013.01); *B01L 2400/084* (2013.01); *C12Q 2600/16* (2013.01)

(56) References Cited

U.S. PATENT DOCUMENTS

| | | | |
|---|---|---|---|
| 2002/0051971 | A1 | 5/2002 | Stuelpnagel et al. |
| 2003/0138941 | A1 | 7/2003 | Gong et al. |
| 2004/0091399 | A1 | 5/2004 | Chung et al. |
| 2005/0252773 | A1* | 11/2005 | McBride ............... B01L 3/5025 204/450 |

OTHER PUBLICATIONS

Written Opinion for PCT/SB2013/000423, 5 pages (dated Dec. 2, 2013).

\* cited by examiner

MICROFLUIDIC DEVICE

SEQUENCE LISTING

In accordance with 37 CFR § 1.52(e)(5), a Sequence Listing in the form of a text file (entitled "Sequence Listing.txt," created Mar. 29, 2016 and 2 KB in size) is incorporated herein by reference in its entirety.

FIELD OF THE INVENTION

The present invention relates to the field of biochemical and biomedical engineering, in particular microfluidic devices and microfluidic devices for detection of biochemical molecules.

BACKGROUND OF THE INVENTION

Delayed diagnoses of diseases are a major concern in hospitals. For example, a delayed diagnosis of multi-drug resistant bacteria (MDRB) may lead to heightened mortality and morbidity because these bacteria are highly contagious and the rate of infection of these bacteria exponentially increases in a matter of hours. The treatment and hospitalization of patients due to, delayed diagnoses also pose a huge economic burden to the healthcare industry. Furthermore, centralized hospitals, in particular, face huge logistic and economic burden where typically more than 300 patients are screened daily for pathogens, such as methicillin-resistant *Staphylococcus aureus* (MRSA) pathogens.

For example, MRSA infections cost the US healthcare system in excess of US$20 billion dollars annually. The problem is further exacerbated by a rapidly increasing rate of MRSA infections, accounting for 60% of *Staphylococcus aureus* infections in 2004 as compared to 22% in 1995. In Singapore's public hospitals, patients infected with MRSA bacteria are 10 times more likely to die during hospitalization as compared to uninfected patients. These patients also stayed 4.6 times longer in hospital and faced four times higher hospital-related costs.

Apart from saving lives, rapid detection of pathogens enables healthcare staff to undertake mitigating measures in a timely manner, such as quarantining patients and determining an effective treatment regime.

Current phenotypic methods of diagnosis are slow, ranging from 18-24 hours or even longer for certain diseases, for example about 4-6 weeks for tuberculosis. This is because such phenotypic methods of diagnosis, such as antimicrobial susceptibility testing for accurate detection of MRSA, are very much dependent on the growth rate of bacterial culture. Thus, these methods typically take as long as 1-4 days, during which time the rate of infection and patient mortality would increase significantly. Therefore, the existing phenotypic approach needs to be complemented with a method for detecting resistant genes, such as polymerase chain reaction (PCR) or real-time PCR. Even though the presence of a target-resistant gene may not confer phenotypic resistance and novel resistant genes will not be detected, PCR is undoubtedly a rapid and sensitive assay for detecting known target-resistant genes.

However, PCR has to be conducted in a highly multiplexed manner, given the sheer number of resistant genes implicated in any given bacterial species. For example, in the case of MRSA infections, healthcare providers are not only interested in the presence of the principal resistant gene, which is mecA, but in addition to that, they would like to ascertain the presence of bacterial and species-specific control genes, such as 16SrRNA and nuc, as well as other antibiotic-resistant genes, such as ermA, blaZ and msrA. In fact, there are well over 20 target genes of interest for MRSA infections alone.

Administering the right treatment is also as critical a task as detecting the presence of pathogens. For example, conventional wisdom suggests the use of broad-spectrum antibiotics for treatment of MRSA infections, in the absence of an antibiotic resistance profile. However, there are disadvantages to the use of broad-spectrum antibiotics. Furthermore, new treatments, such as the use of bacteriophages, require further studies to show that they work in an in vivo setting. As for now, narrow spectrum antibiotics are widely viewed as a viable treatment option for MRSA infections provided the patient is rapidly screened for all relevant antibiotic-resistant genes using PCR.

In the screening of antibiotic-resistant genes using PCR, performing multiple singleplexed PCR reactions is not a viable option for two reasons. Firstly, this significantly increases the number of PCR reactions per patient, and therefore limits the number of patient samples that can be processed simultaneously. Secondly, the sensitivity of the assay is also adversely affected given that patient sample, which is limited to a single nasal swab with no culturing step involved, has to be split over several reactions. Further, as mentioned above, there are multiple target genes to be screened. On the other hand, a multiplexed PCR would address these concerns since multiple antibiotic-resistant target genes will be amplified in a single PCR reaction, effectively increasing patient throughput by multiple folds.

Real-time PCR enables multiplexed detection. However, the number of target genes detected is low, typically ranging from 1 to 3, and in some cases, 4 to 5 targets. The low multiplexing is mainly due to the limitation in the number of fluorescence-conjugated DNA probes that are optically separable. Consequently, the emission bandwidth is effectively limited to 500-700 nm. Furthermore, there is significant overlap between the excitation and emission spectra of organic fluorophores, typically attached at the 5' end of the DNA probes.

Alternatively, instead of real-time PCR, end-point multiplexed PCR assays may also be a viable option since only the presence or absence of resistance genes are needed to be determined.

Multiplexed PCR incorporates multiple primer pairs in a single reaction where each primer pair amplifies a certain target gene. Gene amplification is then followed by an end-point detection assay, such as gel electrophoresis and melt-curve analysis, using a DNA binding dye to confirm the presence of the target gene. Target genes are usually detected based on the size (gel electrophoresis) or melting temperature (melt-curve analysis) of the respective amplicons. However, such detection methods have limited specificity since amplicons of two different target genes may have similar size and/or melt temperature, or alternatively, the sizes and melt temperatures may be too close in value such that the amplicons may not be accurately resolved. Such scenarios are highly likely in a highly multiplexed assay whereby a large number of target genes are detected. Also, gel electrophoresis is highly time-consuming and labor-intensive.

DNA microarray is seen as a viable end-point detection assay where multiplexed PCR is first performed to generate single-stranded amplicons, followed by hybridization of amplicons to sequence-specific probes immobilized on a chip. However, the workflow is time-consuming and labor-intensive, whereby the chip is incubated with the PCR product for several hours, followed by a series of washing steps. Surface treatment of the chip is also required to immobilize the probes onto the chip surface and to ensure DNA localization at the probe spots during incubation. The high equipment cost is another concern since robotics technology is used for spotting probes onto the chip surface, and the optical setup incorporates a scanner for transitioning from one field of view to another so as to cover the entire chip area.

DNA sequencing is another platform technology that enables sequencing of the genome and analysis to determine if known mutations or resistant determinants are present. However, DNA sequencing is still a time-consuming process that may take several days, and there is also a compromise between sequencing speed and sequencing errors that may arise. DNA purification is a key precursor to DNA sequencing, but it is also a limiting factor for rapid diagnosis of bacterial infection and antibiotic resistance since overnight culturing is first performed to obtain pure species-specific bacterial colonies from which DNA is extracted.

Lastly, newer sequencing technologies may substantially reduce sequencing time, but the costs associated with purchasing these machines and running the assays remain high.

There is therefore a need to provide a device and system that overcomes, or at least ameliorates, one or more of the disadvantages described above. There is a need for a rapid, high-throughput and accurate method of detecting target molecules.

SUMMARY OF THE DISCLOSURE

In a first aspect, there is provided a microfluidic device comprising: a plurality of wells, each well having an inlet and an outlet, wherein the inlets are in fluid communication with one or more entry channels and the outlets are in fluid communication with one or more exit channels, wherein said outlet is connected to the exit channel via an outlet connecting channel and said inlet is, connected to the entry channel via an inlet connecting channel wherein the dimension of the outlet connecting channel is configured such that the surface tension of a liquid comprised in the well prevents the release of the liquid through the outlet connecting channel.

In a second aspect, there is provided a system comprising: a microfluidic device as disclosed herein; and a detection device arranged above or below the microfluidic device for detecting a signal emitted by the possible reaction products comprised in the wells during use.

In a third aspect, there is provided a method of detecting at least one target molecule from a liquid sample using the system as disclosed herein, wherein the method sequentially comprises: filling the plurality of wells with the liquid sample by pumping the liquid sample from the source comprising the possible target molecule into the entry channel at a flow rate selected to allow inflow of the liquid sample into the plurality of wells while avoiding release of the liquid into the exit channel, removing excess liquid in the entry channel by pulling a vacuum from the vacuum source connected to the entry channel, pumping sealant into the entry channel followed by pumping sealant into the exit channel to thereby isolate the liquid sample in each well, and detecting a possible signal emitted by a reaction product between the target molecule and the detection probe.

In a fourth aspect, there is provided the use of the system as disclosed herein in the detection of bacteria resistant against at least one antibacterial agent.

BRIEF DESCRIPTION OF THE DRAWINGS

The invention will be better understood with reference to the detailed description when considered in conjunction with the non-limiting examples and the accompanying drawings, in which:

FIGS. 9A to 9C demonstrate that hybridization between the MB probes and the target genes are highly specific and that there is an absence of cross talk between neighboring wells immediately adjacent to the wells with preloaded MB probes.

FIG. 10 confirms that the fluorescence read-out from the probe corresponding to the target of interest is significantly higher than that for the two non-targets.

FIG. 12 shows that the positive control has a significantly higher fluorescence signal at the corresponding wells as compared to the no-template control.

In the figures, like numerals denote like parts.

DETAILED DESCRIPTION OF THE PRESENT DISCLOSURE

In embodiments, there is provided a microfluidic device comprising: a plurality of wells, each well having an inlet and an outlet, wherein the inlets are in fluid communication with one or more entry channels and the outlets are in fluid communication with one or more exit channels, wherein said outlet is connected to the exit channel via an outlet connecting channel and said inlet is connected to the entry channel via an inlet connecting channel wherein the dimension of the outlet connecting channel is configured such that the surface tension of a liquid comprised in the well prevents the release of the liquid through the outlet connecting channel.

Advantageously, the use of the surface tension of liquid, which is an inherent property of the liquid, eliminates the need for the complicated designs required in prior art microfluidic devices. The disclosed device thus possesses an economic advantage when compared to prior art microfluidic devices due to its simplicity in design.

The term "fluid communication" as used herein may refer to the communication of liquid or gas. The liquid referred to herein may be a solution, such as an aqueous solution.

In examples, liquid may be introduced into the wells through the one or more entry channels. In an example, the device comprises only one entry channel such that liquid is introduced into the plurality of wells through the one entry channel. In another example, the device comprises a plurality of entry channels such that liquid is introduced into each well through one entry channel. The entry channels may be separated from each other or interconnected with each other.

The entry channel is in fluid communication with the inlet of the well via the inlet connecting channel. Thus, the liquid in the entry channel may flow through the inlet connecting channel to enter the well via the inlet.

In examples, liquid may be removed from the wells through the one or more exit channels. In an example, the device comprises only one exit channel. In other examples, liquid may be removed from the wells through the one or more entry channels. In such examples, liquid may be introduced into one end of the entry channel and removed from the other end of the entry channel.

The exit channel is in fluid communication with the outlet of the well via the outlet connecting channel. Thus, the liquid in the well may flow out of the well via the outlet and through the outlet connecting channel into the exit channel. The exit channels may be separated from each other or interconnected with each other.

Advantageously, introduction of the liquid into the plurality of wells is simple and straight forward.

Figure 1A:
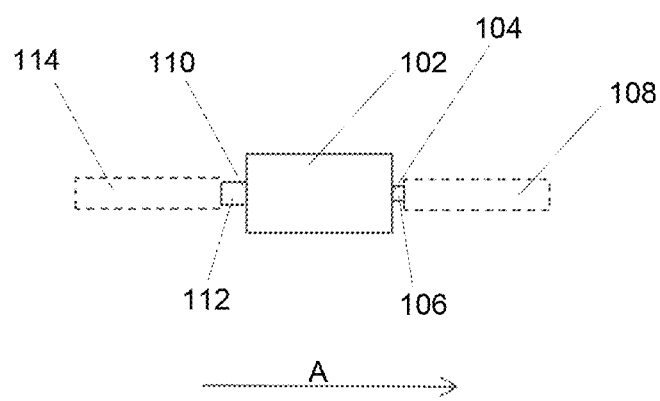
FIG. 1a shows an illustration of the top view of each well according to a specific example of the present disclosure.
Figure 1B:
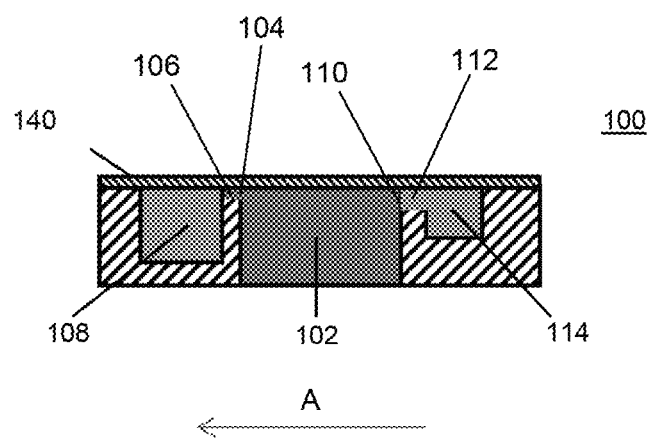
FIG. 1b shows an illustration of the cross-sectional view of the well in the disclosed microfluidic.

An illustration of the top view of each well according to a specific example of the present disclosure is shown in FIG. 1a, while an illustration of the cross-sectional view of the well in the disclosed microfluidic device 100 is shown in FIG. 1b. Well 102 has an inlet 110 and an outlet 104. The inlet 110 is in fluid communication with the entry channel 114 via the inlet connecting channel 112. The outlet 104 is in fluid communication with the exit channel 108 via the outlet connecting channel 106. Liquid flows through the well 102 in the direction of arrow A. Liquid may enter entry channel 114 in the direction of arrow A. Alternatively, liquid may enter entry channel 114 in the direction perpendicular to arrow A where the device comprises only one entry channel. Liquid may be removed from exit channel 108 in the direction of arrow A. Alternatively, liquid may be removed from exit channel 108 in the direction perpendicular to arrow A where the device comprises only one exit channel.

The geometry of the well may not be particularly limited. For example, the well may be substantially cylindrical or substantially cuboid in geometry. The geometry of the entry or exit channel may not be particularly limited. The entry channel may be substantially cylindrical or substantially cuboid in geometry. In an example as seen from FIG. 1b, the well 102 may have the shape of a blind hole with a flat and smooth bottom surface and is linked at the top of the well to the entry channel 114 on one side and exit channel 108 on the other side via the inlet connecting channel 112 and outlet connecting channel 106, respectively. The entry channel 114 and exit channel 108 may also have a flat bottom surface and a square cross-sectional shape.

As illustrated in FIG. 1b, the microfluidic device may be a substrate that comprises a plurality of holes forming the plurality of wells. The substrate may also comprise grooves extending along a length of the substrate forming the entry channel on one side of the wells and grooves extending along a length of the substrate forming the exit channel on the other side of the wells. The substrate may also comprise an orifice between the entry or exit channel and the well to form the inlet connecting channel or outlet connecting channel, respectively.

In examples, the entry channel connects all the inlets of the plurality of wells with each other. The liquid flowing through the entry channel may therefore enter the plurality of wells in sequence. For example, liquid will enter the well located nearest to the beginning of the fluid flow, followed by the next well and so on.

In examples, the exit channel connects all the outlets of the plurality of wells with each other. The liquid flowing out from each well therefore enters the exit channel.

To aid in the flow of liquid, a positive or negative pressure may be applied. The positive pressure applied may be from a pump or syringe whereby liquid is pumped or injected into the device. Alternatively, gas may be pumped or injected to provide a positive pressure. The negative pressure applied may be from a vacuum source. Where a vacuum source is used, a liquid trap may be provided before the vacuum source to prevent liquid from entering the vacuum source.

To aid in the flow of liquid in the entry channel, a positive pressure may be applied at one end of the entry channel to push the liquid or a negative pressure may be applied at the other end of the entry channel to pull the liquid or both a positive pressure and a negative pressure are applied accordingly to move the liquid towards the end where the negative pressure is applied. To provide a positive pressure at one end of the entry channel, liquid may be pumped into that end of the entry channel. Alternatively, liquid may be injected into that end of the entry channel by a syringe. A source of liquid may be in fluid communication with a first end of the entry channel. The liquid source may be a chamber, tube or syringe filled with the liquid which is pumped or injected into the first end of the entry channel. A source of gas may be in fluid communication with a first end of the entry channel. The gas source may be a syringe filled with the gas which is injected into the first end of the entry channel to push the liquid through the entry channel. The gas may be an inert gas that does not react with the liquid or may be air. To provide a negative pressure at the other end of the entry channel, a vacuum may be applied using, for example, a syringe. A vacuum source may be in fluid communication with a second end of the entry channel. The vacuum source may be connected to an end of the entry channel via a liquid trap.

In an example, to aid the flow of liquid from the entry channel into the well, a negative pressure may be pulled at the exit channel.

To aid the flow of liquid from the well into the exit channel, a positive pressure may be applied at one end of the exit channel to push the liquid or applying a negative pressure at the other end of the exit channel to pull the liquid or applying both a positive pressure and a negative pressure accordingly to move the liquid towards the end where the negative pressure is applied. To provide a positive pressure at one end of the exit channel, a source of gas may be in fluid communication with a first end of the exit channel. A gas source may be a syringe filled with the gas which is injected into the first end of the exit channel to push the liquid through the exit channel. The gas may be an inert gas that does not react with the liquid or may be air. To provide a negative pressure at the other end of the exit channel, a vacuum may be applied using, for example, a syringe. In an example, a vacuum may be applied using, for example, a syringe. A vacuum source may be in fluid communication with a second end of the exit channel. The vacuum source may be connected to an end of the exit channel via a liquid trap.

As liquid enters the well through the inlet connecting channel and inlet, the liquid is retained within the well due to the dimension of the outlet connecting channel. The dimension of the outlet connecting channel may be configured to prevent release of the liquid out of the well during filling. Due to the configuration of the dimension of the outlet connecting channel, the surface tension of the liquid comprised in the well at the outlet connecting channel during filling is higher than the pressure that pushes the liquid into the exit channel. The pressure that pushes the liquid into the exit channel may be dependent on the pressure difference between air and liquid, which may be related to the filling speed, the dimensions of the various channels and other parameters. The filling speed is the flow rate of the liquid during the filling step as described herein.

The term "surface tension" as used herein refers to the tension at the separation surface between the liquid and the surface of the outlet connecting channel, i.e. the liquid-solid interface. The surface tension characterizes the ability of the liquid to wet the surface of the outlet connecting channel. When a liquid wets a surface, the liquid substantially spreads across the surface. Generally, if the contact angle between a liquid droplet and the surface is greater than 90°, there is high surface tension at the liquid-solid interface and the liquid is not released out of the well into the exit channel. Conversely, if the contact angle between a liquid droplet and the surface is smaller than 90°, there is low surface tension at the liquid-solid interface and the liquid is released out of the well into the exit channel. In an example, when the contact angle between the liquid and the surface of the outlet connecting channel is smaller than 90°, the liquid is released out of the well during filling.

When the pressure on the liquid in the well increases until the pressure is substantially equal to the surface tension of the liquid at the outlet connecting channel, the well may be substantially completely filled, for example 90% or 95% or 99% or 100% of the volume of the well is filled. Introduction of liquid into the device may then be halted. In an example, when the pressure on the liquid is higher than the surface tension of the liquid at the outlet connecting channel, liquid is released into the exit channel.

Excess liquid in the entry channel may be removed by applying a positive pressure at a first end of the entry channel to push the liquid out of the second end of the entry channel. The positive pressure may be in the form of a pumped or injected gas. Alternatively, a negative pressure may be applied at the second end of the entry channel to pull the liquid or both a positive pressure and a negative pressure are applied accordingly to move the liquid towards the end where the negative pressure is applied. Any excess liquid in the exit channel may likewise be removed.

Figure 2:
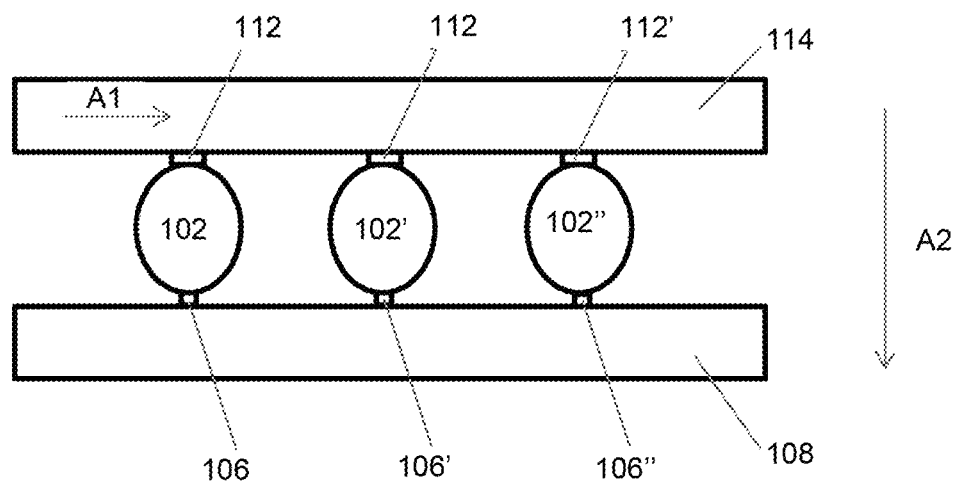
FIG. 2 shows an illustration of the top view of part of the disclosed device according to a specific example of the present disclosure.

An illustration of the top view of part of the disclosed device according to a specific example of the present disclosure is shown in FIG. 2. Liquid flows through entry channel 114 in the direction of arrow A1 and enters well 102 first. While well 102 is being filled with liquid, the dimension of the outlet connecting channel 106 prevents liquid in well 102 from exiting into exit channel 108. When well 102 is substantially completely filled, the liquid flow is directed to the second well 102'. During filling of well 102', the dimension of the outlet connecting channel 106' prevents liquid in well 102' from exiting into exit channel 108. After filling of well 102' is completed, the liquid flow is directed to the third well 102". Whether the incoming liquid breaks into the exit channel from one filled well, e.g. well 102, or continues filling into an unfilled well, e.g. well 102', depends on the relative resistance of the two wells. The relative resistance is dependent on the design of the disclosed microfluidic device. In an example, due to the dimension of the outlet connecting channels, the liquid in all the wells will not break into the exit channel until all the wells are substantially completely filled. In another example, due to the dimension of the outlet connecting channel and the dimension of the entry channel, the liquid in all the wells will not break into the exit channel until all the wells are substantially completely filled. If the dimension of the outlet connecting channel is sufficiently small and the dimension of the entry channel is sufficiently large, such that the relative resistance to exit the well is higher than the relative resistance to enter the next well, the incoming liquid may not break from the filled well into the exit channel and instead, may continue filling the next well. Conversely, if the dimension of the outlet connecting channel is not small enough while the dimension of the entry channel is too narrow, such that the relative resistance to exit the well is lower than the relative resistance to enter the next well, there may be a risk that the incoming liquid will break into the exit channel before all the wells are filled.

The dimension of the entry channel may therefore be configured in relation to the dimension of the outlet connecting channel such that all the wells are substantially completely filled before liquid comprised in the wells is released through the outlet connecting channel into the exit channel. The cross-section of the entry channel may be between about 0.5 mm to 1 mm by between about 0.5 mm to 1 mm. The diameter or width of the entry channel may be between about 0.5 mm to 1 mm, or about 0.6 mm to 1 mm, or about 0.7 mm to 1 mm, or about 0.5 mm to 0.9 mm, or about 0.5 mm to 0.8 mm. The depth of the entry channel may be between about 0.5 mm to 1 mm, or about 0.6 mm to 1 mm, or about 0.7 mm to 1 mm, or about 0.5 mm to 0.9 mm, or about 0.5 mm to 0.8 mm. In an example, the width of the entry channel is 0.6 mm and the depth of the entry channel is 0.5 mm. Further, since excess liquid in the entry channel may not be utilized and be removed, the entry channel may be configured to be small in dimension to minimize wastage of liquid.

The exit channel may be configured to be larger in dimension than that of the entry channel to minimize flow resistance of liquid being removed or a sealant being introduced. The cross-section of the exit channel may be between about 0.7 mm to 1.5 mm by between about 0.5 mm to 1.5 mm. The diameter or width of the exit channel may be between about 0.7 mm to 1.5 mm, or about 0.8 mm to 1.5 mm, or about 0.9 mm to 1.5 mm, or about 1 mm to 1.5 mm, or about 1.1 mm to 1.5 mm, or about 1.2 mm to 1.5 mm, or about 0.7 mm to 1.4 mm, or about 0.7 mm to 1.2 mm, or about 0.7 mm to 1 mm. The depth of the exit channel may be between about 0.5 mm to 1.5 mm, or about 0.6 mm to 1.5 mm, or about 0.7 mm to 1.5 mm, or about 0.8 mm to 1.5 mm, or about 0.9 mm to 1.5 mm, or about 0.5 mm to 1.3 mm, or about 0.5 mm to 1.1 mm, or about 0.5 mm to 0.9 mm. In an example, the width of the exit channel is 1 mm and the depth of the exit channel is 0.7 mm.

Figure 1C:
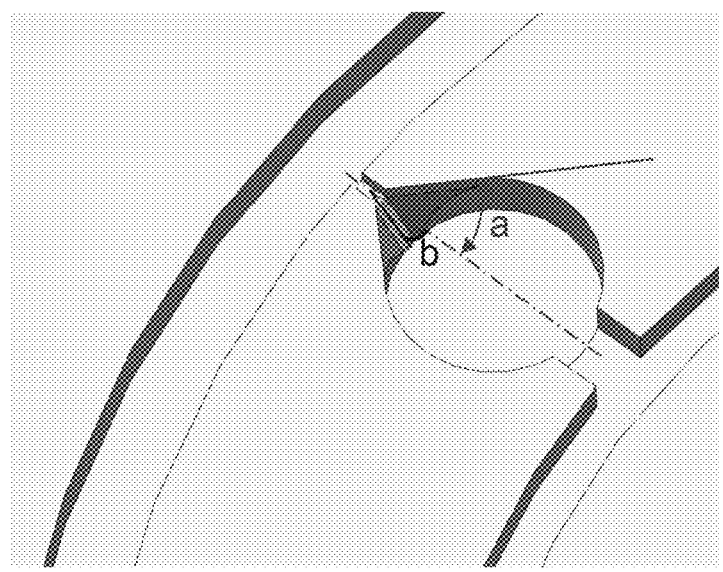
FIG. 1c shows an illustration of the top view of well 102 connected to exit channel 108 via outlet connecting channel 106 comprising a converging zone.

The dimension of the outlet connecting channel may be small enough relative to the dimension of the well in order to provide sufficient surface tension to stop the liquid from entering the exit channel. As mentioned above, the dimension of the outlet connecting channel may be sufficiently small as compared to the dimension of the entry channel to prevent liquid from releasing into the outlet connecting channel before the remaining wells are filled with liquid. The dimension of the outlet connecting channel may be smaller than that of the entry channel. The dimension or cross-section of the outlet connecting channel may be between about 0.05 mm to 3 mm by between about 0.05 mm to 3 mm. Where the outlet connecting channel has a cylindrical geometry, the diameter of the outlet connecting channel may be between about 0.05 mm to 3 mm, or about 0.1 mm to 3 mm, or about 0.1 mm to 1.5 mm, or about 0.2 mm to 3 mm, or about 0.2 mm to 2.5 mm, or about 0.2 mm to 2 mm, or about 0.2 mm to 1.5 mm, or about 0.3 mm to 3 mm, or about 0.3 mm to 2.5 mm, or about 0.3 mm to 2 mm, or about 0.3 mm to 1.5 mm, or about 0.4 mm to 3 mm, or about 0.4 mm to 2.5 mm, or about 0.4 mm to 2 mm, or about 0.4 mm to 1.5 mm, or about 0.5 mm to 3 mm, or about 0.5 mm to 2.5 mm, or about 0.5 mm to 2 mm, or about 0.5 mm to 1.5 mm, or about 0.8 mm to 3 mm, or about 0.8 mm to 2.5 mm, or about 0.8 mm to 2 mm, or about 0.8 mm to 1.5 mm, or about 0.1 mm to 1 mm, or about 0.1 mm to 0.8 mm, or about 0.1 mm to 0.5 mm, or about 0.1 mm to 0.4 mm, or about 0.1 mm to 0.3 mm. Where the outlet connecting channel has a rectangular geometry, the length of the outlet connecting channel may be between about 0.05 mm to 3 mm, or about 0.1 mm to 3 mm, or about 0.1 mm to 1.5 mm, or about 0.2 mm to 3 mm, or about 0.2 mm to 2.5 mm, or about 0.2 mm to 2 mm, or about 0.2 min to 1.5 mm, or about 0.3 mm to 3 mm, or about 0.3 mm to 2.5 mm, or about 0.3 mm to 2 mm, or about 0.3 mm to 1.5 mm, or about 0.4 mm to 3 mm, or about 0.4 mm to 2.5 mm, or about 0.4 mm to 2 mm, or about 0.4 mm to 1.5 mm, or about 0.5 mm to 3 mm, or about 0.5 mm to 2.5 mm, or about 0.5 mm to 2 mm, or about 0.5 mm to 1.5 mm, or about 0.8 mm to 3 mm, or about 0.8 mm to 2.5 mm, or about 0.8 mm to 2 mm, or about 0.8 mm to 1.5 mm, or about 0.1 mm to 1 mm, or about 0.1 mm to 0.8 mm, or about 0.1 mm to 0.5 mm, or about 0.1 mm to 0.4 mm, or about 0.1 mm to 0.3 mm; and the breadth of the outlet connecting channel may be between about 0.05 mm to 3 mm, or about 0.1 mm to 3 mm, or about 0.1 mm to 1.5 mm, or about 0.2 mm to 3 mm, or about 0.2 mm to 2.5 mm, or about 0.2 mm to 2 mm, or about 0.2 mm to 1.5 mm, or about 0.3 mm to 3 mm, or about 0.3 mm to 2.5 mm, or about 0.3 mm to 2 mm, or about 0.3 mm to 1.5 mm, or about 0.4 mm to 3 mm, or about 0.4 mm to 2.5 mm, or about 0.4 mm to 2 mm, or about 0.4 mm to 1.5 mm, or about 0.5 mm to 3 mm, or about 0.5 mm to 2.5 mm, or about 0.5 mm to 2 mm, or about 0.5 mm to 1.5 mm, or about 0.8 mm to 3 mm, or about 0.8 mm to 2.5 mm, or about 0.8 mm to 2 mm, or about 0.8 mm to 1.5 mm, or about 0.1 mm to 1 mm, or about 0.1 mm to 0.8 mm, or about 0.1 mm to 0.5 mm, or about 0.1 mm to 0.4 mm, or about 0.1 mm to 0.3 mm. The depth of the outlet connecting channel may be between about 0.2 mm to 0.5 mm, or about 0.3 mm to 0.5 mm, or about 0.4 mm to 0.5 mm, or about 0.2 mm to 0.4 mm, or about 0.2 mm to 0.3 mm. In an example, the dimension or cross-section of the outlet connecting channel is 0.2 mm by 0.2 mm. In another example, the cross-section of the outlet connecting channel is 0.2 mm by 0.2 mm and the length of the outlet connecting channel is 0.35 mm. The outlet connecting channel may comprise of a converging zone that connects the wells to the outlet connecting channel smoothly. The converging zone may have an angle (angle a) measured from the longitudinal axis through the outlet connecting channel to the side wall of the converging zone of between about 30 degrees to 60 degrees, e.g. 45 degrees, and an angle (angle b) measured from the bottom of the well to the bottom of the outlet connecting channel of between about 40 degrees to 70 degrees, e.g. 56 degrees. The converging zone of outlet connecting channel 106 is illustrated in FIG. 1c where the angle of the converging zone to the side wall of the outlet connecting channel is denoted as angle a, which may be 45 degrees, and the angle of the converging zone to the bottom of the outlet connecting channel is denoted as angle b, which may be 56 degrees.

The term "diameter" refers to the maximum length of an object. For objects having an irregular shape, the diameter is the length of the longest cross section of the object.

The diameter of the well may be between about 1 mm to 4 mm, or about 1.5 mm to 4 mm, or about 1.7 mm to 4 mm, or about 2 mm to 4 mm, or about 2.2 mm to 4 mm, or about 2.5 mm to 4 mm, or about 3 mm to 4 mm, or about 1 mm to 3 mm, or about 1 mm to 2.5 mm, or about 1 mm to 2.2 mm, or about 1 mm to 2 mm, or about 1.5 mm to 3 mm, or about 2 mm to 3 mm, or about 2 mm to 2.5 mm; and the depth or height of the well may be between about 0.5 mm to 1.5 mm, or about 0.6 mm to 1.5 mm, or about 0.7 mm to 1.5 mm, or about 0.8 mm to 1.5 mm, or about 0.9 mm to 1.5 mm, or about 1 mm to 1.5 mm, or about 0.5 mm to 1 mm, or about 0.5 mm to 0.9 mm, or about 0.5 mm to 0.8 mm, or about 0.8 mm to 1 mm.

The diameter and the depth of the well may be adjusted to suit the application of the microfluidic device. In instances, it is advantageous to reduce the volume of the well. The volume of the well may be between about 1 µL to 10 µL, 2 µL to 10 µL, or about 2 µL to 5 µL, or about 3 µL to 5 µL. In an example, the diameter of the well may be reduced to 2 mm and the depth of the well may be reduced to 1 mm to reduce the volume of the well to 3.1 µL.

The plurality of wells may be in the range of between about 2 to more than 100, or about 2 to 100, or about 5 to 100, or about 10 to 100, or about 5 to 50. In an example, there are 31 wells. Accordingly, the total liquid volume comprised in the device may be between about 30 µL to 100 µL, or about 30 µL to about 90 µL, or about 40 µL to about 70 µL. In an example, there are 10 wells comprised in the disclosed device with a total liquid volume of about 46 µL. Advantageously, the total liquid volume of the disclosed device may be a fraction of that required in prior art devices. For example, the total liquid volume of the disclosed device having 10 wells is about 20% of the total volume required in 10 conventional PCR tubes. The total liquid volume may further be reduced by re-introducing the excess liquid that was removed from the entry channel. The total liquid volume here includes the volume of the wells and the volume of the liquid in the entry channel.

The dimension of the inlet connecting channel may be configured such that inflow of the liquid into the well is not prevented by the surface tension of the liquid. The dimension of the inlet connecting channel may be large enough relative to the dimension of the entry channel such that inflow of the liquid into the well is not prevented by the surface tension of the liquid, and that liquid in the well does not come out during filling.

In examples, the plurality of wells can only be accessed via the entry channel and exit channel. In examples, the well can be isolated by preventing access via the entry channel and exit channel. By "isolate", it is meant that a particular species or substance is separated from a mixture, sample or biological specimen. Advantageously, liquid in the well after isolation may not be lost to the environment, e.g. by evaporation. Further advantageously, after isolation, the liquid contained in each well will not contaminate liquid in other wells. The occurrence of stray signal emission leading to false-positive emission readings may also be reduced. In an example, there is no occurrence of false positives or false negatives.

A sealant may be used to isolate the liquid in a well. The sealant may be introduced into the entry channel or exit channel to seal and isolate the liquid in the well. The sealant may be pumped or injected into an end of the entry channel or an end of the exit channel. The sealant may also be introduced from a sealant source into an end of the entry channel or an end of the exit channel by applying a vacuum at the other end of the entry channel or exit channel. The sealant source may be in fluid communication with an end of the entry channel or an end of the exit channel. The sealant source may be a tube or chamber filled with the sealant.

The sealant may be any type of substance that can at least partially block or prevent leakage of the liquid in the well to effectively isolate the liquid in the well. By "effective", it is meant that the liquid in the well, including the liquid in the inlet connecting channel and the outlet connecting channel, is sufficiently separated from the mixture, sample or specimen outside the well, e.g. in the entry or exit channels. The sealant may be any type of material that has a lower rate of vaporization than the liquid in the well. The sealant may be any type of material that is immiscible with the liquid in the well. The sealant may be any type of material that does not allow vapor of the liquid in the well to pass through. The sealant may be wax, polymers, gelatin, gum, starch, or a derivative thereof.

In an example, the sealant may be liquid wax. The term "wax" as used herein includes naturally occurring fatty acid esters such as carnauba, candelilla, beeswax, etc., mineral oil and other organic materials which have the physical character of waxes, such as polyethylenes, paraffins, ozokerites, etc. Paraffin wax is generally used to define hard, crystalline wax commonly obtained from petroleum distillates, derived from mineral oils of the mixed base or paraffin base type and may include materials such as higher boiling distillate waxes and microcrystalline wax. In an example, the liquid wax is Chill-Out™ liquid wax from Bio-Rad Laboratories Inc., CA, USA.

In examples, each well may comprise a detection probe. The term "detection probe" generally refers to, a molecule capable of binding to a target molecule, where "detection probe" may encompass probe molecules immobilized to a support or probe molecules not immobilized to a support. The detection probe may be immobilized to a support including a surface, a film, or a particle. In an example, the detection probe is not immobilized to a support. The steric hindrance of immobilized probes may thus be avoided.

The detection probe may be capable of binding to at least a portion of the target molecule, e.g. a specific sequence of a target nucleic acid, via covalent bonding, hydrogen bonding, electrostatic bonding, or other attractive interactions, so as to detect the target molecule. In an example, the detection probe may be a protein which binds to the target molecule which may also be a protein. Therefore, the binding in this example is via protein-protein interactions to detect, for example, a conformational change in the protein structure. In another example, the detection probe may be a nucleic acid which binds to the target molecule which may also be a nucleic acid. Therefore, the binding in this example is via hybridization so as to detect, for example, the presence or absence of a target nucleic acid or the presence of a single nucleotide mutation in the nucleic acid. The reaction product between the target molecule and the detection probe may emit a signal which can be detected via a detection system.

The term "target nucleic acid", as used herein, refers to a nucleic acid sequence comprising a sequence region which may bind to a complementary region of the detection probe. The target nucleic acid sequence may be amplified and when hybridized with the complementary region of the detection probe, it may be possible to detect the presence or absence of the target nucleic acids and the quantitative amount of the target nucleic acids. The term "hybridization" as used in this application, refers to the ability of two completely or partially complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G) on single nucleic acid strands, base pairing can form between bases who are not members of these "canonical"

pairs. Non-canonical base pairing is well-known in the art. See e.g., The Biochemistry of the Nucleic Acids (Adams et al., eds., 1992).

The detection probe may be coupled to a detection means, such as a label, for measuring hybridization of a target to the detection probe. The label may be a radioactive isotope or a fluorophore. In an example, each detection probe may be conjugated with a different fluorophore so that the different probes can be distinguished.

In examples, the detection probe comprises DNA or RNA. In other examples, the detection probe comprises single-stranded polynucleotides having a hairpin loop structure capable of forming a double-stranded complex with a region of a sample polynucleotide. In an example, the detection probe is a molecular beacon (MB) probe comprising a fluorophore and a quencher. Advantageously, the MB probe does not require any further modification prior to its use. Further advantageously, no additional monovalent or divalent salts or additives, such as bovine serum albumin (BSA), are required for the detection assay. In the absence of a target molecule, the MB probe remains in a stable hairpin conformation such that fluorescence from the fluorophore is totally quenched due to the proximity of the fluorophore at one end of the polynucleotide and the quencher at the other end of the polynucleotide. For example, proximity of the 6-carboxyfluorescein (6-FAM) fluorophore at the 5' end of the MB probe with Black Hole Quencher-1 (BHQ1) at the 3' end quenches any fluorescence. In the presence of a target molecule, a portion of the probe hybridizes to a complementary sequence of the target molecule, resulting in the separation of the fluorophore and the quencher and subsequently resulting in the emission of fluorescence from the fluorophore.

In examples, the target molecule comprises DNA or RNA. In examples, the target molecule comprises a gene of interest. In an example, the gene of interest may be genes that confer resistance against anti-viral or anti-bacterial treatment, such as treatment with one or more antibiotics. In another example, the gene of interest may be bacterial and species-specific control genes. In a particular example, the genes of interest are 16SrRNA and nuc. In another particular example, the genes of interest are mecA, ermA, blaZ and msrA.

Advantageously, the reaction between the detection probe and the target molecule is substantially instantaneous at room temperature, e.g. 30° C. The targets of interest may hybridize with the respective detection probes where the signal emitted is achieved with little noise at an optimal temperature of 30° C. Further advantageously, there is no need for any incubation of the probe and target to result in a reaction product. There is also no need for any washing before or after the possible reaction. Where the detection of the presence or absence of the target gene is required, there is advantageously no need for melt curve analyses and the associated equipment.

In examples, the detection probe is a lyophilized detection probe. Advantageously, the lyophilization of a detection probe avoids the need for immobilization of the detection probe to a support Immobilization of the detection probe is required when a washing step to remove unbound detection probes is required. However, in an example, a washing step is not required since a signal is emitted only when the detection probe is bound to the target molecule. Furthermore, the need for robotic intervention to provide the detection probe can also be avoided. The well may be pre-loaded with the detection probe prior to the introduction of liquid or sample. The pre-loaded detection probe may be lyophilized within each well. The reaction between a possible target molecule and the detection probe pre-loaded in the well may thus be instantaneous after the sample comprising the possible target molecule is introduced into the well.

The well may be pre-loaded with probes in an amount that balances the baseline hybridization intensity. In an example, the well may be pre-loaded with probes in an amount of between about 0.5 pmol/well to 7 pmol/well. The concentration of probes required may be dependent on the target molecules. To enhance fluorescence intensity and uniformity, the concentration of the probes can be optimized. Advantageously, such optimization is not possible in conventional microarray methods where loading capacity on the solid support is limited.

In examples, each well comprises a unique sequence-specific detection probe. Each unique detection probe may bind specifically to a different target molecule. Advantageously, each well may be capable of detecting a particular target of interest and therefore, the disclosed device is capable of detecting as many target molecules as the number of wells.

In examples, the target molecule is the product of an amplification reaction. An amplification reaction results in an increase in the concentration of a nucleic acid molecule relative to its initial concentration by a template-dependent process. The term "template-dependent process" refers to a process that involves the template-dependent extension of a primer molecule. Amplification methods include, but are not limited to polymerase chain reaction (PCR), DNA ligase chain reaction and other amplification reactions well known to persons skilled in the art. The components of an amplification reaction include reagents used to amplify a target nucleic acid, for example, amplification primers, a polynucleotide template, deoxyribonucleotide triphosphate, polymerase and nucleotides.

In an example, asymmetric PCR or LATE PCR are used. Asymmetric PCR preferentially amplifies one DNA strand in a double-stranded DNA template. Advantageously, high-throughput can be achieved since the target molecule is amplified by a highly multiplexed asymmetric PCR reaction. Further advantageously, the amplified product does not require any further modification to attach any functional groups or fluorophores.

The present approach involves the distribution of amplified product into an array of wells where a high degree of multiplexing can be achieved since each well having a sequence-specific detection probe therein is capable of detecting a particular target of interest instantaneously.

In an example, the liquid referred to hereinabove is a solution comprising the target molecule or possibly comprising the target molecule. The solution may be a biological sample, e.g. a cheek swab, taken from a subject to detect the presence or absence of specific genes.

The concentration of the target molecule in the sample may be lower than 0.01 ng/$\mu$L, or lower than 0.005 ng/$\mu$L, or lower than 0.004 ng/$\mu$L, or lower than 0.003 ng/$\mu$L, or lower than 0.002 ng/$\mu$L, or lower than 0.001 ng/$\mu$L.

In examples, a sealant is used to isolate the solution in the well. In an example where the sealant is not used, the solution in the wells evaporates when the microfluidic device is heated. This is because the air surrounding the solution promotes evaporation. Where evaporation takes place, the intensity of the signal emitted by the reaction product between the detection probe and the target molecule in the solution, e.g. fluorescence, may be decreased. Attenuation of fluorescence intensity may occur at temperatures as low as 40° C. to 50° C. When the microfluidic device is heated to more than about 95° C., significant bubble formation in the sealant and the solution may be observed, adversely affecting fluorescence quantification. Thus, the use of a sealant is advantageous.

Therefore, in examples, the entry channel is in fluid communication with the following, including, but not limited to, a vacuum source connected to a first end of the entry channel or a vacuum source connected to a first end of the entry channel via a liquid trap, a sealant source connected to a second end of the entry channel, a gas source connected to the second end of the entry channel and a source comprising a possible target molecule connected to the second end of the entry channel. In examples, the exit channel is in fluid communication with the following, including, but not limited to, a vacuum source connected to a first end of the exit channel or a vacuum source connected to a first end of the exit channel via a liquid trap and a sealant source connected to a second end of the exit channel. In all examples, the connection of the entry or exit channels to the various sources is controlled by one or more valves which can be controlled separately. The valves may be electromagnetic or rotary valves. The control of the valves may be automated, thereby facilitating the transport of the various fluids within the device. For example, the automated delivery of target molecules into the respective wells for hybridization with the sequence-specific detection probes can be facilitated.

Figure 4A:
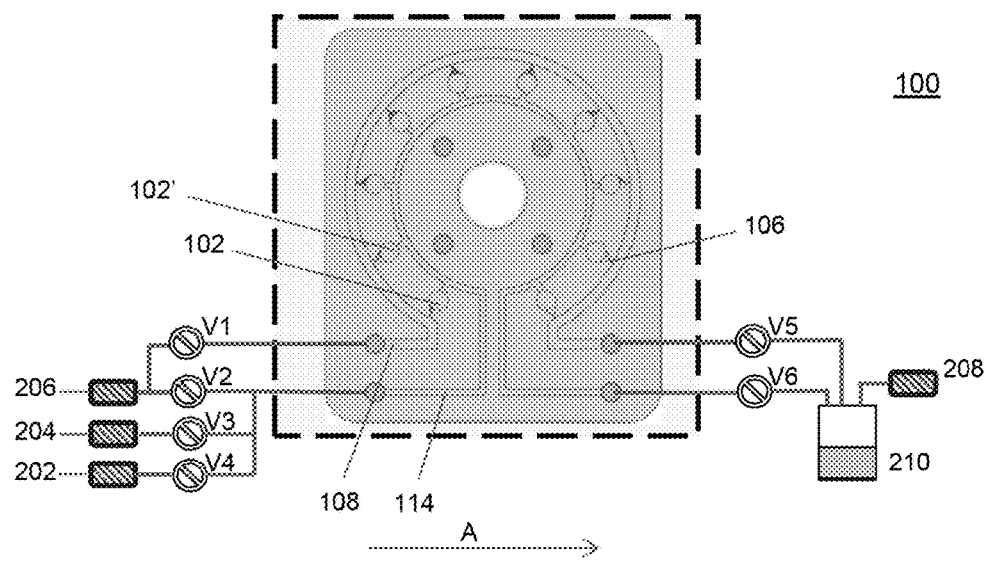
FIG. 4a shows an illustration of the device 100 according to a specific example of the present disclosure where the plurality of wells 102 is arranged in a circular configuration.
Figure 4B:
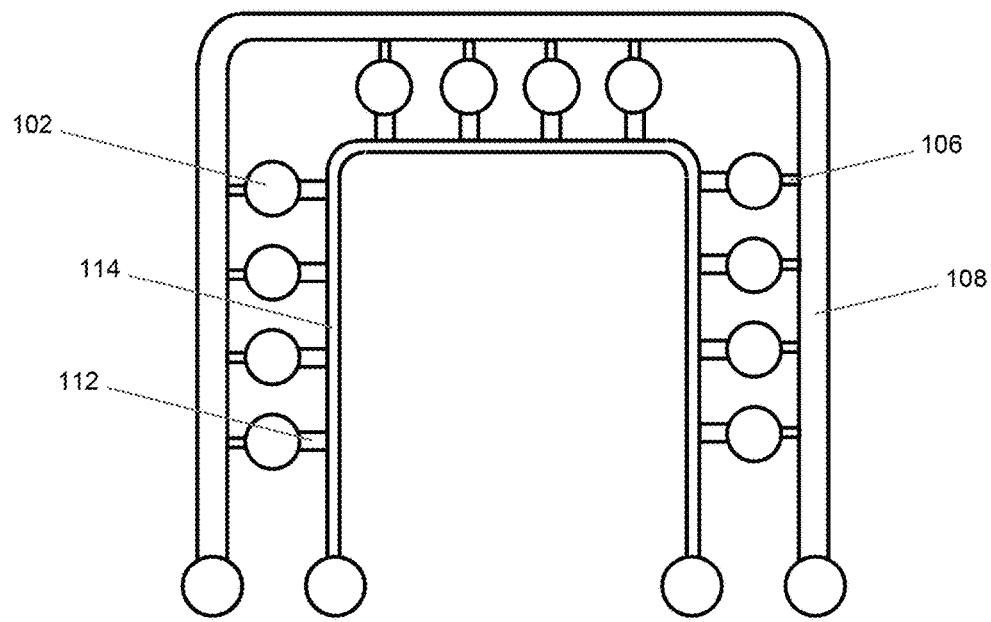
FIG. 4b shows an illustration of the device 100 according to another specific example of the present disclosure where the plurality of wells 102 is arranged in a square configuration.

An illustration of the device 100 according to a specific example of the present disclosure is shown in FIG. 4a. The plurality of wells in this example is arranged in a circular configuration. The amplified PCR product 202 is introduced along the entry channel 114, entering the wells sequentially, i.e. well 102, followed by well 102', etc. To aid the flow of product 202, an air source 204 provides, air at a first end of the entry channel 114 to push the product 202 through the channel, while a vacuum source 208 provides a vacuum at a second end of the entry channel 114 to pull the product through the channel. The general direction of liquid movement is in the direction of arrow A. The vacuum source 208 is connected to the second end of the entry channel 114 via a liquid trap 210 to prevent any excess liquid from entering the vacuum source. When the plurality of wells 102 are completely filled with the PCR product 202, excess PCR product is removed from the entry channel 114 in order to prevent cross-talk between different wells, e.g. by the diffusion of preloaded detection probes from one well to another. Both the entry and exit channels are filled with liquid wax from a liquid wax source 206 to seal the PCR product 202 in the wells 102, thus preventing sample evaporation. The sources 202, 204, 206 and 208 may be connected to the entry channel 114 or exit channel 108 via tubing with valves. When in use, the PCR product 202 is introduced by opening V4 and V6. After the wells are completely filled, excess product 202 is removed by opening V3 and V6. Liquid wax is introduced into the entry channel 114 to prevent evaporation of the product 202 in the wells 102 by opening V2 and V6. Liquid wax is introduced into the exit channel 108 by opening V1 and V5. An illustration of the device 100 according to another specific example of the present disclosure is shown in FIG. 4b where the plurality of wells 102 is arranged in a square configuration.

The binding of a target molecule to a detection probe may result in a reaction product that emits a signal. In an example, the binding of a target molecule to the detection probe results in the emission of fluorescence. Advantageously, the disclosed device does not require time-consuming incubation, washing or surface modification of the device surface. There may also be no need for coating of the device surface, thereby avoiding any scattering or background fluorescence from the coating material.

Figure 3:
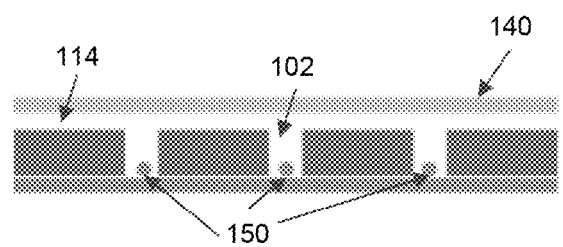
FIG. 3 shows an illustration of the cross-sectional view of molecular beacon probes 150 loaded in each well 102 according to a specific example of the present disclosure.

An illustration of the cross-sectional view of molecular beacon probes 150 loaded in each well 102 according to a specific example of the present disclosure is shown in FIG. 3. The entry channel 114 may deliver biological sample comprising a specific target molecule which will bind only to one of the molecular beacon probes 150 specifically complementary to the target molecule.

The detection of emission of fluorescence represents an end-point PCR detection methodology where the presence or absence of a target molecule can be determined. The disadvantages of real-time PCR may thus be avoided.

The amplification reaction and the detection of the reaction product between the amplified product and the detection probe may be conducted in separate steps. Advantageously, the amplified product is replicated to a sufficiently large number of copies before the amplified product is distributed into the plurality of wells in the microfluidic device. Thus, the multiplexing capability of the disclosed device is simply dependent on the number of wells.

As mentioned herein, the target molecule may be a nucleic acid that confer resistance against antibacterial treatment.

The device may be covered with a cover material to enclose the plurality of wells or channels. The cover material may be compatible with the liquid in the device. An example of such a covering is illustrated as 140 in FIG. 1b and FIG. 3. Alternatively, the device may comprise an enclosure to enclose the plurality of wells or channels. The material enclosing the plurality of wells or channels may be transparent. In an example, the plurality of wells or channels is covered by a thin, transparent tape, e.g. MicroAmp™ optical adhesive film which is PCR compatible, DNA/RNA/RNase-free from Applied Biosystems, California, USA. The remaining parts of the device may be made of a translucent material or a non-transparent material.

The device may be made of a material that does not inhibit the binding of the detection probe with the target molecule. The material may be poly(methyl methacrylate) (PMMA), polycarbonate (PC), polypropylene (PP), polyethylene, polyvinyl alcohol, acrylonitrile butadiene styrene or polystyrene. Advantageously, the device may be compatible with common PCR reagents found on the market, e.g. PCR master mixes from Qiagen, Netherlands (Taq PCR Master Mix Kit), Promega, Wis., USA (GoTaq Hot Start Colorless Master Mix) and Invitrogen, CA, USA (Platinum PCR SuperMix).

Figure 5:
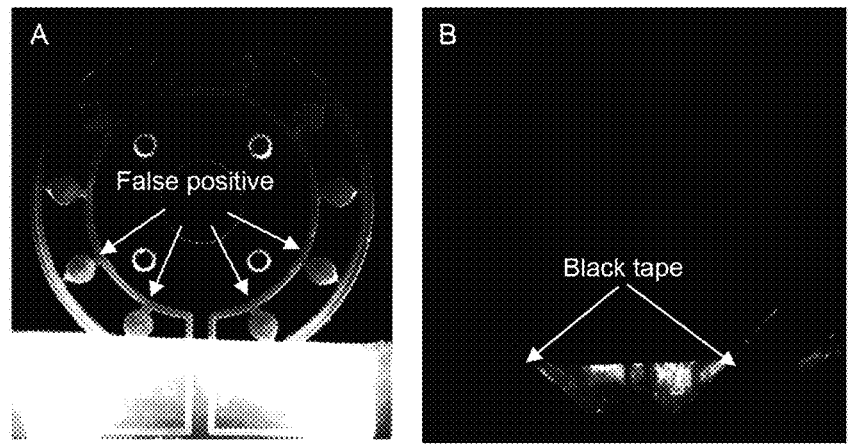
FIG. 5A shows an image of the disclosed device when adhesive is used. The image demonstrates that fluorescence can be seen where adhesive is used, in addition to the source and within the wells and channels.
FIG. 5B shows an image of the disclosed device having black tape covering the area where adhesive was placed, evidencing that the black tape effectively reduces the autofluorescence previous emitted by the adhesive.

The cover material may also be an opaque material or additionally covered by a translucent material or an opaque material. In an example, the opaque material is black tape. Advantageously, the opaque material reduces or prevents background signal emissions which may interfere with the signal emitted from the reaction product between the detection probe and the target molecule. In an example, the transparent adhesive used to cover the plurality of wells or channels is a source of green autofluorescence, which may overlap with the fluorescence emission band of the detection probe, resulting in false-positive signals within the wells and channels. FIG. 5A shows an image of the disclosed device demonstrating fluorescence at the bottom of the image from the source and within the wells and channels where adhesive was placed. FIG. 5B shows an image of the disclosed device having black tape covering the area where adhesive was placed. When comparing FIGS. 5A and 5B, it is clear that the black tape effectively reduces the autofluorescence previous emitted by the adhesive.

The entry channel and exit channel may be secured to the microfluidic device by O-rings.

When liquid wax is used as the sealant, it may also emit autofluorescence. However, its emission wavelength is blue, and can hence be easily filtered off. Further, the detection probe may emit low to almost no autofluorescence.

In an embodiment, there is provided a system comprising the disclosed microfluidic device. The system may include a detection device arranged above or below the disclosed microfluidic device for detecting a signal emitted by the possible reaction products comprised in the wells during use.

The detection device may be an optical system. The optical system may comprise a light source and filters that are capable of capturing the signal emitted by the reaction product of the detection probe and the target molecule. The light source may be an ultraviolet-visible (UV-Vis) broad band mercury/LED light source and the filters may be excitation, emission and dichroic filters, each having compatible wavelength bands targeting 6-FAM fluorophore of the MB probes. Such filters can be obtained from Semrock Inc., New York, USA. The light source may be capable of illuminating the microfluidic device so that a camera can capture an image of the possible signal emitted. The light source and the filters comprised in the detection device may also be capable of emitting a signal to excite the reaction product to generate fluorescence by the lens and the camera. An example of a suitable camera is the Grasshopper2 CCD-based red-green-blue (RGB) camera obtained from Point, Grey Research Inc., Richmond BC, Canada, with a 25-mm focus lens obtained from Edmund Optics, NJ, USA. The image captured by the camera may be processed by a processing program. For example, a customized image analysis software from Matlab Image Acquisition Toolbox, The Mathworks Inc., MA, USA, can be used. The processing program may be administered by a processor, such as a computer. Advantageously, the optical system provides a non-motorized setup for one-shot imaging of emitted signals, such as fluorescence.

The plurality of wells comprised in the disclosed microfluidic device may be arranged to be in thermal communication with a heating element. The system may comprise a heating module so that an end-point melt curve analysis of the reaction product between the possible target molecule and the detection probe can be performed. Advantageously, single- or multiple-point mutations in the target sequence can be detected. In an example, the system does not comprise the heating module if only the detection of the presence or absence of the target gene is required. Single nucleotide polymorphism (SNP) may also be detected without the need for melt curve analysis. In an example, the detection probe is sensitive to SNPs where a single base pair mismatch between the probe and DNA sequence results in a lower fluorescence intensity compared to a complete match. In this example, the probe may be lyophilized with a wild type/normal sequence in one well (well A) and a probe with a mutant sequence comprising a SNP in another well (well B). If the amplified product has a wild type sequence, well A will register a higher fluorescence intensity as compared to well B. Conversely, if the amplified product has a mutant sequence comprising the SNP, well B will register a higher fluorescence intensity as compared to well A. Advantageously, the lack of a heating module allows the disclosed system to be compact and cost-effective. Further advantageously, the disclosed system may possess specificity and sensitivity comparable to prior art systems. The end-point hybridization of the detection probes to the target molecules directly occurring on the microfluidic device may have comparable detection sensitivity to an end-point hybridization of the same detection probes in a real-time amplification reaction. Advantageously, the disclosed system may be able to detect DNA concentrations as low as 0.002 ng/µL. The specificity of the disclosed system may be attributed to the sequence-specific detection probes used and therefore, melt curve analysis is not required.

The heating module may be a Peltier heating module. The heating module may comprise a fan, a thermoelectric (TE) heater/cooler (e.g. 9501/127/030 from FerroTec, CA, USA), and a TE control kit (e.g. from FerroTec, CA, USA). The TE control kit may comprise an amplifier (e.g. FTA600 H-bridge amplifier from FerroTec, CA, USA) and a temperature controller (e.g. FTC100 temperature controller from FerroTec, CA, USA). The TE heater may be powered by the amplifier, which is controlled by the temperature controller. A T-type thermocouple (e.g. 5TC-TT-T-40-36, OMEGA Engineering, CT, USA) may be mounted on the TE heater to measure the temperature, and may be used as a feedback to the temperature controller. The temperature difference between the TE heater and actual temperature inside the well may be calibrated by measuring the temperature inside the well directly with equal volumes of PCR product.

Figure 6:
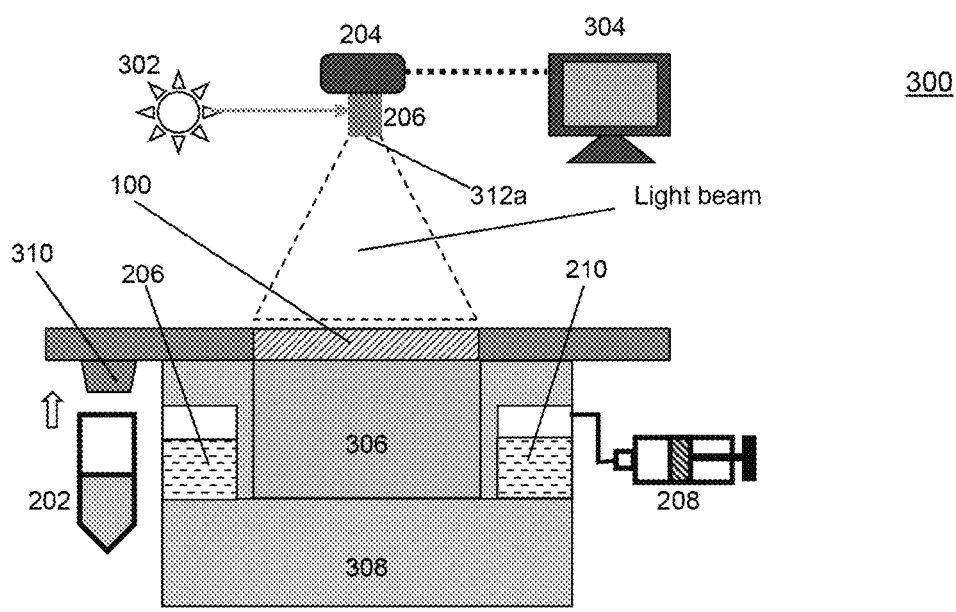
FIG. 6 shows an illustration of the system 300 in accordance with a specific example of the present disclosure.

An illustration of the system 300 in accordance with a specific example of the present disclosure is shown in FIG. 6. The light source 303 from the CCD camera 204 equipped with a lens 206 casts a conically shaped light beam onto the microfluidic device 100. The CCD camera 204 is linked to computer 304 Liquid wax in a container 206 is provided and connected to the device 100 via a tubing (not shown). A tube 202 containing PCR product is also provided and is connectable to the device 100 via a sampling port 310. A vacuum source in the form of a syringe pump 208 is provided together with liquid trap 210. Device 100 may be heated by a heater 306 controlled by temperature controller 308. When in use, the microfluidic device 100 preloaded with MB probes (not shown) is inserted onto the top of heater 306. The tube 202 containing the PCR products solution is attached to the sampling port 310 and the PCR products are delivered to the wells by control of valves (not shown) and the vacuum generated by the syringe pump 208. The PCR products are then sealed in the wells by liquid wax from container 206 which fill both the entry and exit channels (not shown) of the microfluidic device 100. According to the program preset in the temperature controller 308, the heater 306 raises the temperature of the PCR mixture in the wells in steps, sinking at each temperature for several minutes. During this several minutes, the excitation light beam from the light source 302 illuminates all the wells on the device 100, and the generated fluorescence is captured by the lens and the CCD camera. The image data is then sent to the computer for further processing to provide the results for optical detection.

In an example, the light beam generated from the light source may be enclosed by an insulator to prevent loss of light energy to the surroundings. Advantageously, fluorescence imaging may thereby be facilitated. The insulator may be configured in a shape according to the shape of the light beam. In an example, the insulator is a conically shaped and directly connectable to the lens of the camera. The connections may be threaded connections. In an example, the insulator has a C-mount male thread being 4 mm in length, the thread being 1 inch in diameter and having 32 threads per inch, while the lens has a corresponding female thread. The distance between the lens and the microfluidic device may be adjusted such that the beam of light reaching the device is sufficient to cover the plurality of wells. In an example, the distance between the lens and the microfluidic device may be adjusted such that the beam of light reaching the device is sufficient to cover a 96-well plate.

Figure 7A:
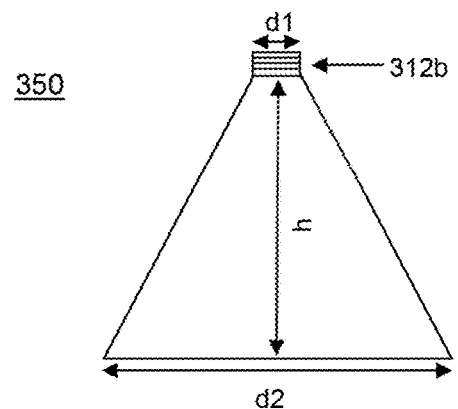
FIG. 7a shows a schematic of the light insulator 350 in accordance with an example of the present disclosure.
Figure 7B:
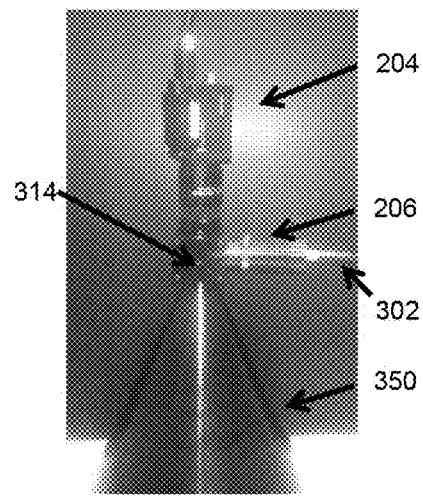
FIG. 7b shows a photograph of a prototype of the optical system that incorporates the light insulator 350.

A schematic of the light insulator 350 in accordance with an example of the present disclosure is shown in FIG. 7a. A male thread 312b having a diameter of d1 of the light insulator 350 is directly connectable to the corresponding female thread 312a of the camera lens (shown in FIG. 6). The distance (h) between the lens and the microfluidic device is about 25 cm and the diameter (d2) of the beam of light is about 21.2 cm. FIG. 7b shows a photograph of a prototype of the optical system that incorporates the light insulator 350. The optical system comprises the camera 204 and the light source 302 connected to a filter 314 by a collimating optics lens 206. The optical system is mounted directly above the light insulator 350 via a C-mount interface (not shown).

Figure 7C:
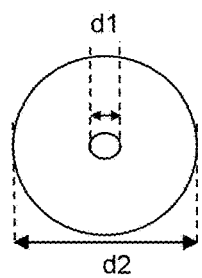
FIG. 7c shows a schematic of the beam of light in a circular pattern from the light source incident on the plurality of wells on the microfluidic device.

The beam of light from the light source, either with or without the insulator, incident on the plurality of wells on the microfluidic device may be of a circular pattern as shown in FIG. 7c. The diameter of the light incident on the device is d2, which is the diameter of the insulator, when used. As the insulator has a connection for connecting to the lens, there will not be any incident light below the connection. Accordingly, there will be a dark spot at the central region of the incident light having a diameter d1 substantially equal to the diameter of the connection.

In examples, the plurality of wells is arranged on the microfluidic device in a pattern to ensure that the incident light is substantially uniform across all the wells. Due to the dark spot in the central region of the incident light, the plurality of wells may be arranged around the dark spot, e.g. in a symmetrical pattern around the dark spot. The wells may be arranged in a square pattern around the dark spot or in a circular pattern around the dark spot. In an example, the plurality of wells is arranged in a radially symmetrical pattern around the dark spot. Advantageously, the excitation of the detection probes may substantially be uniform across all wells since the excitation light from the light source also has a radially symmetrical distribution when projected on the surface of the microfluidic device. This advantageously enables the one-shot imaging of the entire device, thereby avoiding the need for an optical scanner to conduct multiple scans of each well. This tremendously decreases the complexity and cost of the disclosed system. The compact size of the microfluidic device also advantageously enables all wells to be imaged in a single field of view.

Figure 8:
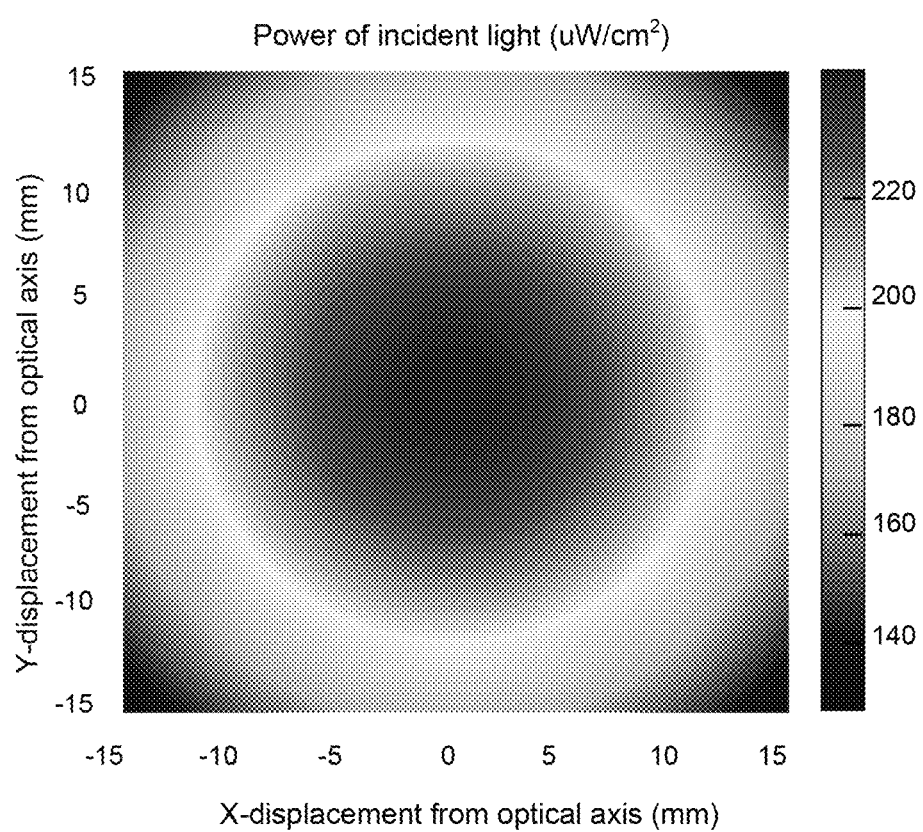
FIG. 8 shows the distribution of light incident on the surface of the microfluidic device having a radial symmetry.

FIG. 8 confirms that the distribution of light incident on the surface of the microfluidic device has a radial symmetry. The distribution has a radial symmetry centered around the optical axis at (0,0).

The system may comprise a sealant source, as described above, connectable to the device to be in fluid communication with an end of the entry channel or an end of the exit channel or an end of the entry and exit channels.

The system may comprise a gas source, as described above, connectable to the device to be in fluid communication with an end of the entry channel.

The system may comprise a source comprising a possible target molecule, as described above, connectable to the device to be in fluid communication with an end of the entry channel.

The system may comprise a vacuum source, as described above, connected to an end of the exit channel or an end of the entry channel or an end of the entry and exit channel. The system may comprise a vacuum source connected to an end of the exit channel or an end of the entry channel or an end of the entry and exit channel via a liquid trap, as described above.

In an embodiment, there is provided a method of detecting at least one target molecule from a liquid sample using the system disclosed herein, wherein the method sequentially comprises: filling the plurality of wells with the liquid sample by pumping the liquid sample from the source comprising the possible target molecule into the entry channel at a flow rate selected to allow inflow of the liquid sample into the plurality of wells while avoiding release of the liquid into the exit channel, removing excess liquid in the entry channel by pulling a vacuum from the vacuum source connected to the entry channel, pumping sealant into the entry channel followed by pumping sealant into the exit channel to thereby isolate the liquid sample in each well, and detecting a possible signal emitted by a reaction product between the target molecule and the detection probe.

In examples, the steps are performed sequentially.

The plurality of wells may be sequentially filled with the liquid sample, as described herein. The target molecule may be the reaction product of an amplification reaction, as described herein. The amplification reaction may be a reaction as described herein, e.g. an asymmetric PCR.

During the filling step, the liquid sample may be pumped from the sample source through the entry channel at a flow rate selected so that the liquid sample does not enter the exit channel before all the wells are filled. The liquid sample may be pumped from the sample source through the entry channel at a flow rate of between about 10 mL/h to 120 mL/h, or about 10 mL/h to 100 mL/h, or about 10 mL/h to 80 mL/h, or about 10 mL/h to 60 mL/h, or about 30 mL/h to 120 mL/h, or about 30 mL/h to 100 mL/h, or about 30 mL/h to 80 mL/h, to fill the wells. In an example, the flow rate is between about 10 mL/h to 100 mL/h. In an example, the flow rate is 40 to 60 mL/h. Advantageously, the range of flow rates provides a stable filling operation. If the flow rates are higher than the upper limit, the filling operation becomes unstable, resulting in some wells not being filled or not being completely filled. The range of flow rates may be achieved by pulling a vacuum from the vacuum source connected to the exit channel.

During the filling step, the perturbation to the detection probe in the well may compensate the absence of mixing or vortexing of the mixture of the detection probe and the target molecule. Advantageously, the perturbation may be sufficient for reconstituting the probes and quantifying the resulting fluorescence signal from any given well.

During the removal step, excess liquid may be removed from the entry channel by pulling a vacuum from the vacuum source connected to one end of the entry channel. A gas may be introduced from the gas source connected to the other end of the entry channel to aid in the removal of excess liquid. The flow rate of the removal step may be higher than the flow rate of the filling step. In an example, the liquid may be removed from the entry channel at a flow rate of 140 mL/h. In another example, the liquid may be removed from the entry channel at a flow rate of between about 10 mL/h to 140 mL/h, or about 10 mL/h to 120 mL/h, or about 10 mL/h to 100 mL/h, or about 10 mL/h to 80 mL/h, or about 30 mL/h to 140 mL/h, or about 30 mL/h to 120 mL/h, or about 30 mL/h to 100 mL/h, or about 50 mL/h to 140 mL/h, or about 50 mL/h to 120 mL/h. In an example, the flow rate is 40 to 60 mL/h.

The step of pumping the sealant into the entry channel may be conducted at a flow rate dependent on the dimension of the entry channel. The step of pumping the sealant into the entry channel may be conducted at a flow rate of between about 10 mL/h to 40 mL/h, or about 10 mL/h to 30 mL/h, or about 20 mL/h to 40 mL/h, or about 20 mL/h to 30 mL/h. In an example, the flow rate is between about 10 mL/h to 20 mL/h to ensure that the introduction of the sealant into the entry channel is stable. In an example, the flow rate is 10 to 15 mL/h.

The step of pumping the sealant into the exit channel may be conducted at a flow rate dependent on the dimension of the exit channel. The step of pumping the sealant into the exit channel may be conducted at a flow rate of between about 10 mL/h to 80 mL/h, or about 10 mL/h to 70 mL/h, or about 10 mL/h to 60 mL/h, or about 20 mL/h to 80 mL/h, or about 20 mL/h to 70 mL/h, or about 30 mL/h to 80 mL/h. In an example, the flow rate is 20 to 40 mL/h. The flow rate of this step may be higher than the flow rate of the step of pumping the sealant into the entry channel due to the larger dimension of the exit channel.

In an example, the step of pumping the sealant into the entry channel is conducted before the step of pumping the sealant into the exit channel to effectively isolate the liquid in the well.

Where the step of pumping the sealant into the exit channel is conducted before the step of pumping liquid wax into the entry channel, an oil/water interface having an interfacial tension of about 44 dynes/cm forms at the well exit. However, in comparison, the surface tension of water at the well exit is about 72.8 dynes/cm at 20° C., much higher than that of the oil/water interface. Thus, the interfacial tension of the oil/water interface at the exit channel may be insufficient to confine the solution within the well when the liquid wax fills the inner channel. The solution may thus enter the exit channel, thereby affecting the accuracy of the optical detection of the wells.

The sealant may be a sealant disclosed herein, such as liquid wax.

The steps may be conducted at room temperature. Advantageously, a convective flow may be created in each well at a temperature of as low as 30° C., thereby aiding in the mixing of the detection probe and the target molecule to produce a completely uniform mixture.

If a melt curve analysis is required, the process may be conducted at a temperature of less than 75° C., or less than 70° C. to prevent bubble formation in the sealant and liquid.

Advantageously, the disclosed method may be completed in less than 1 min, or less than 40 sec, or less than 30 sec, or less than 20 sec, or less than 15 sec, or less, than 12 sec. The entire sample-to-detection workflow may be completed in less than 5 hours, or less than 3 hours, or less than 2 hours. Advantageously, the disclosed method provides a rapid and high-throughput screening of a possible target molecules. The rapid detection of a panel of genes that confer resistance to antibiotic treatment against methicillin-resistant *Staphylococcus aureus* may be provided.

In an embodiment, there is provided the use of the disclosed system in the detection of bacteria resistant against at least one antibacterial agent. The disclosed system may be used in the detection of genes that confer resistance to treatment against anti-viral or antibacterial infections. The bacteria may be methicillin-resistant *Staphylococcus aureus*.

The term "bacterial infection" refers to the invasion of the host mammal by pathogenic bacteria. This includes the excessive growth of bacteria which are normally present in or on the body of a mammal. More generally, a bacterial infection can be any situation in which the presence of a bacterial population(s) is damaging to a host mammal. The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria). In an example, the antibacterial agent is an antibiotic.

The disclosed system may be a viable substitute for the conventional antibiotic susceptibility test performed in hospitals.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

The asymmetric amplification of the DNA target of interest was conducted in this example. The DNA target of interest was the nuc, mecA and blaZ genes.

The forward excess primer for the nuc gene is represented by SEQ ID NO: 1, the reverse limiting primer for the nuc gene is represented by SEQ ID NO: 2 and the MB probe for the nuc gene is represented by 6-FAM-SEQ ID NO: 3-BHQ1.

The forward excess primer for the mecA gene is represented by SEQ ID NO: 4, the reverse limiting primer for the mecA gene is represented by SEQ ID NO: 5 and the MB probe for the mecA gene is represented by 6-FAM-SEQ ID NO: 6-BHQ1.

The forward excess primer for the blaZ gene is represented by SEQ ID NO: 7, the reverse limiting primer for the blaZ gene is represented by SEQ ID NO: 8 and the MB probe for the blaZ gene is represented by 6-FAM-SEQ ID NO: 9-BHQ1.

The multiplexed PCR reaction solution was comprised of 100 µL of excess primer (2 µM) and limiting primer (0.2 µM) for each DNA target of interest, 200 µM of each deoxyribonucleotide triphosphate (dNTP), 2 mM of $MgCl_2$, GoTaq® Hot Start DNA Polymerase in 2× Colorless GoTaq® Reaction Buffer (pH 8.5) and 2 µL of template DNA.

PCR amplification was performed on a PTC 200 thermal cycler (Bio-Rad Laboratories, CA, USA).

An initial denaturation step of 2 min at 95° C. is followed by 60 cycles of 95° C. for 30 sec, 50° C. for 30 sec (annealing step), and 72° C. for 30 sec (annealing step). A final elongation step at 72° C. for 10 min was included at the end of 60 cycles.

Example 2

The uniformity of incident light is possible only if the distribution of light intensity on the plane of the surface of the microfluidic device is radially symmetrical. The radial symmetry of incident light was demonstrated via the following experiment.

A power meter (Model 841-PE, Newport Corp., Irvine, Calif., USA) was used to measure light intensity ($\mu W/cm^2$) incident on the sample plane located 10 cm from the optical fiber (400 µm, 0.75 m UV-SR, Ocean Optics) outlet. A solid-state switchable light source (Lumencor, Spectra Light Engine, Lumencor Inc., Beaverton, Oreg., USA) was employed. The measurements were made at various radial displacements of 0-15 mm from the optical axis.

FIG. 8 confirms that the distribution of light incident on the sample plane, i.e. chip, has a radial symmetry. This ensures that the incident light is uniform across all chip wells, since the wells are arrayed in a radially symmetric pattern.

Example 3

The disclosed microfluidic device was used to detect mecA, nuc and blaZ genes in *Staphylococcus aureus*. The experiment was repeated three times on three devices.

Figure 9:
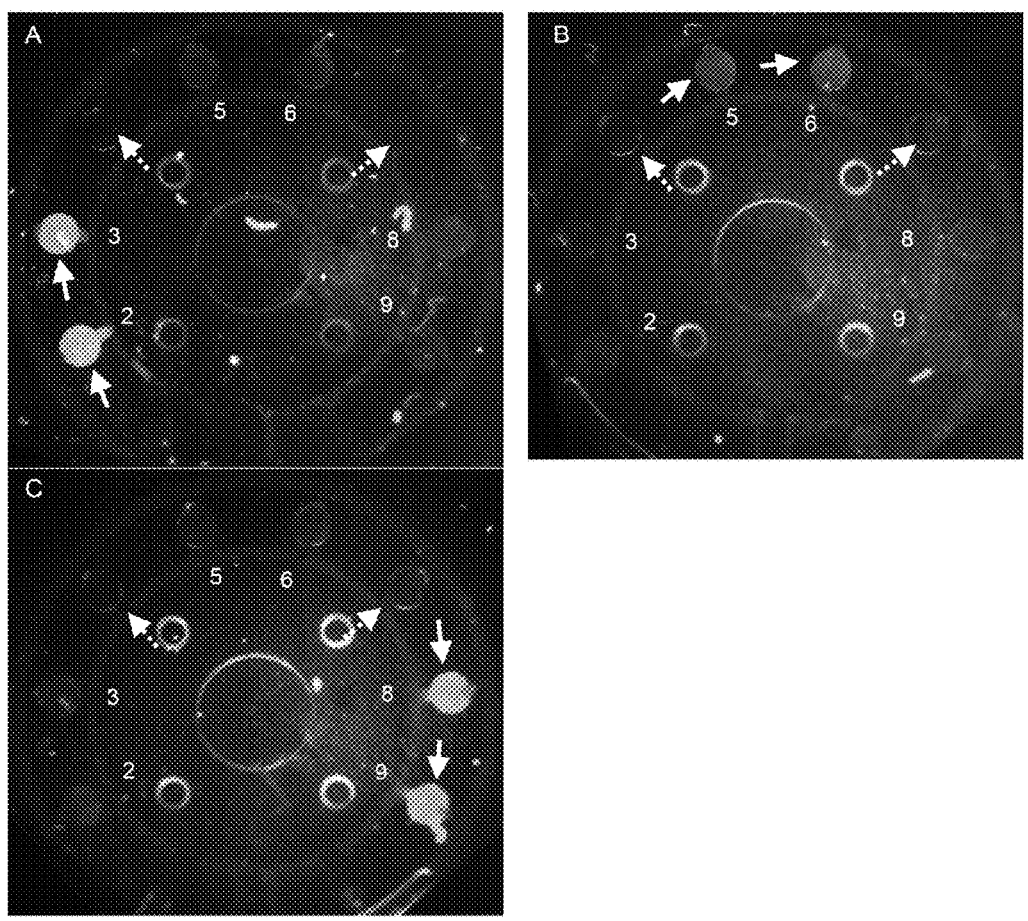
FIG. 9A shows an image of the spontaneous detection of mecA, nuc and blaZ genes in *Staphylococcus aureus* in wells 2-3 in the first device referred to in Example 3.
FIG. 9B shows an image of the spontaneous detection of mecA, nuc and blaZ genes in *Staphylococcus aureus* in wells 5-6 in the second device referred to in Example 3.
FIG. 9C shows an image of the spontaneous detection of mecA, nuc and blaZ genes in *Staphylococcus aureus* in wells 8-9 in the third device referred to in Example 3.

In the first device, mecA-, nuc- and blaZ-specific MB probes were preloaded in wells 2-3 (indicated by solid white arrows in FIG. 9A). In the second device, mecA-, nuc- and blaZ-specific MB probes were preloaded in wells 5-6 (indicated by solid white arrows in FIG. 9B). In the third device, mecA-, nuc- and blaZ-specific MB probes were preloaded in wells 8-9 (indicated by solid white arrows in FIG. 9C). In all three devices, 1.6 pmoles of lyophilized mecA-, nuc- and blaZ-specific MB probes were preloaded into the respective wells.

The mecA, nuc and blaZ targets were amplified separately in asymmetric single-plex PCR reactions, and the single-stranded PCR products were then delivered to the three devices. On delivery of the amplified PCR products, the MB probes would hybridize with their complementary targets, resulting in fluorescence emission at 520 nm under blue light excitation at 488 nm.

FIGS. 9A to 9C show the spontaneous detection of mecA, nuc and blaZ genes in *Staphylococcus aureus* in three devices at room temperature.

As observed in FIGS. 9A to 9C, the detection assay is highly specific. A particular probe emits fluorescence only if its complementary target is present. As seen in FIG. 9A, fluorescence was detected in wells 2-3 where the hybridization between the MB probes and the genes occurred. As seen in FIG. 9B, fluorescence was detected in wells 5-6 where the hybridization between the MB probes and the genes occurred. As seen in FIG. 9C, fluorescence was detected in wells 8-9 where the hybridization between the MB probes and the genes occurred.

Figure 10:
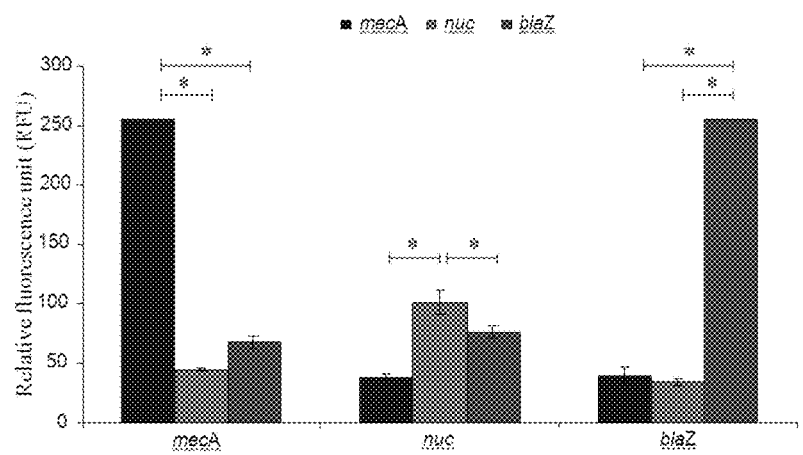
FIG. 10 shows a graph of fluorescence for each target gene in Example 3 in wells 2-3 (for the first set of graphs), wells 5-6 (for the second set of graphs) and wells 8-9 (for the third set of graphs).

FIG. 10 confirms that the fluorescence read-out from the probe corresponding to the target of interest is significantly higher than that for the two non-targets. Although the hybridization signal for the nuc gene is markedly lower than that for the mecA and blaZ genes, it is still significantly higher than that for the other two genes in the presence of its complementary target. In FIG. 10, the "*" represent $p \leq 0.01$.

FIGS. 9A to 9C also confirm the absence of cross talk between neighboring wells. The neighboring wells (indicated by dashed arrows) that are immediately adjacent to the wells with preloaded MB probes show no fluorescence signal. This confirms that there are no carry-over of fluorophores from one well to another.

Example 4

The amount of MB probes on the nuc and mecA hybridization signals were investigated here.

Figure 11A:
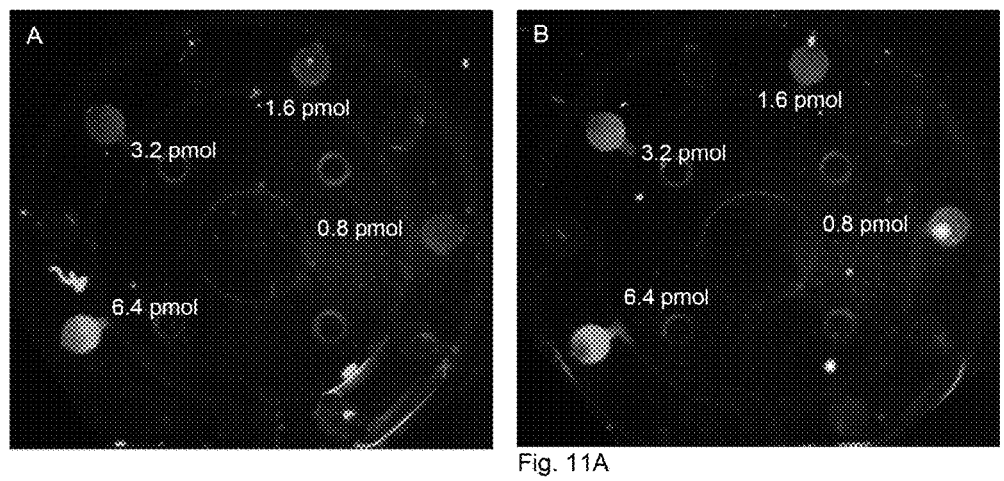
FIGS. 11A and B show images of the detection of nuc and mecA genes, respectively; referred to in Example 4. The hybridization signal intensity increases as the loading concentration of nuc and mecA MB probes, respectively, increases from 0.8 pmol/well to 6.4 pmol/well.
Figure 11B:
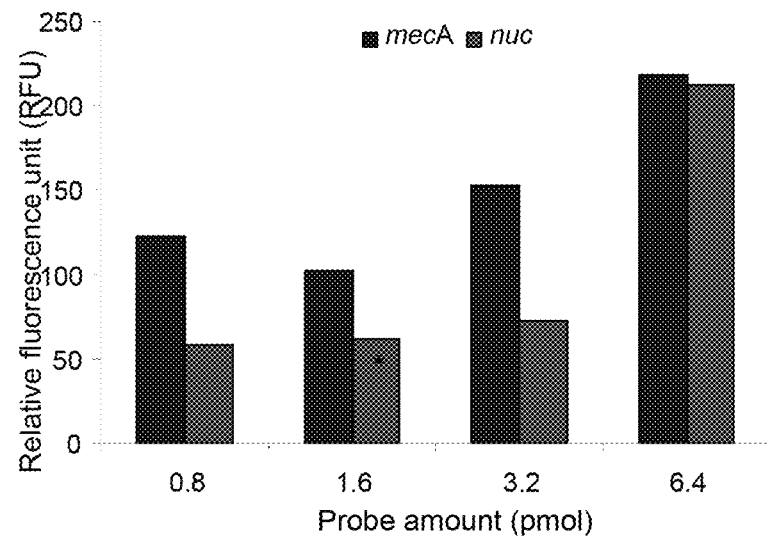

FIGS. 11A-B show an increase in hybridization signal intensity as the loading concentration of nuc and mecA MB probes, respectively, increases from 0.8 pmol/well to 6.4 pmol/well.

This suggests that the amount of complementary ssDNA in the sample may be in excess and therefore, the amount of hybridization increases as the amount of probes increase.

Another suggestion is that ssDNA may have secondary structures that limit the proportion of probes that hybridize to them. The provision of a higher concentration of probes may increase the likelihood of hybridization.

Either way, different targets tend to display different baseline hybridization intensity, which can be adjusted to some degree by varying the MB probe concentration.

Example 5

In this example, the fluorescence of a device comprising a no-template control was compared with a device comprising a positive control.

1.6 pmoles of lyophilized sequence-specific MB probes corresponding to mecA, nuc and blaZ target genes were preloaded in wells 2-3, 5-6 and 8-9 in both devices.

Figure 12:
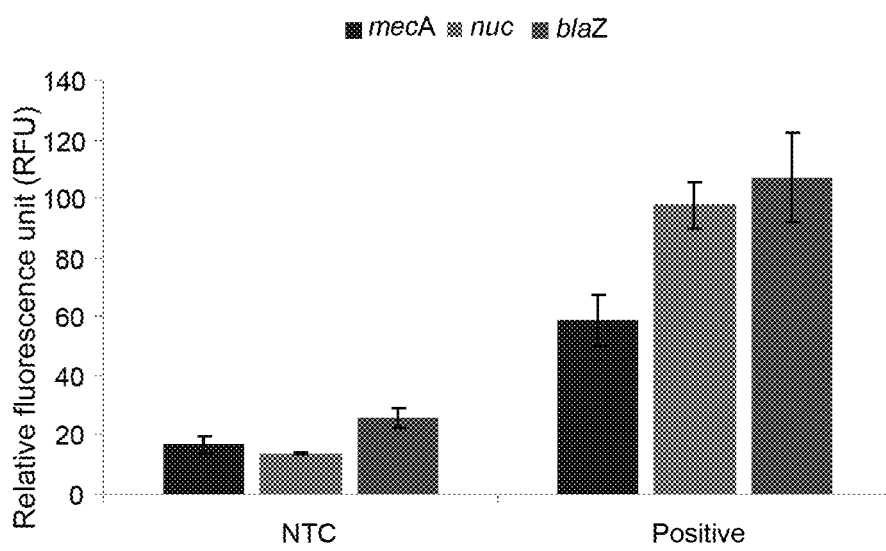
FIG. 12 shows a graph of the fluorescence of a device comprising a no-template control compared with a device comprising a positive control in Example 5. Sequence-specific MB probes corresponding to mecA, nuc and blaZ target genes were preloaded in wells 2-3, 5-6 and 8-9 in both devices.

As expected, the positive control shows a significantly higher fluorescence signal at the corresponding wells as compared to the no-template control (see FIG. 12). Here, a suitable threshold can be easily defined to differentiate a valid hybridization signal from a false positive.

Example 6

In this example, the DNA template concentrations were varied.

The mecA DNA template concentrations were varied at 0 ng/μL (no-template control (NTC)), $2\times10^{-5}$ ng/μL, $2\times10^{-3}$ ng/μL, $2\times10^{-1}$ ng/μL, and $2\times10^{1}$ ng/μL. The MB probe is loaded at 1.6 pmol/well.

Figure 13:
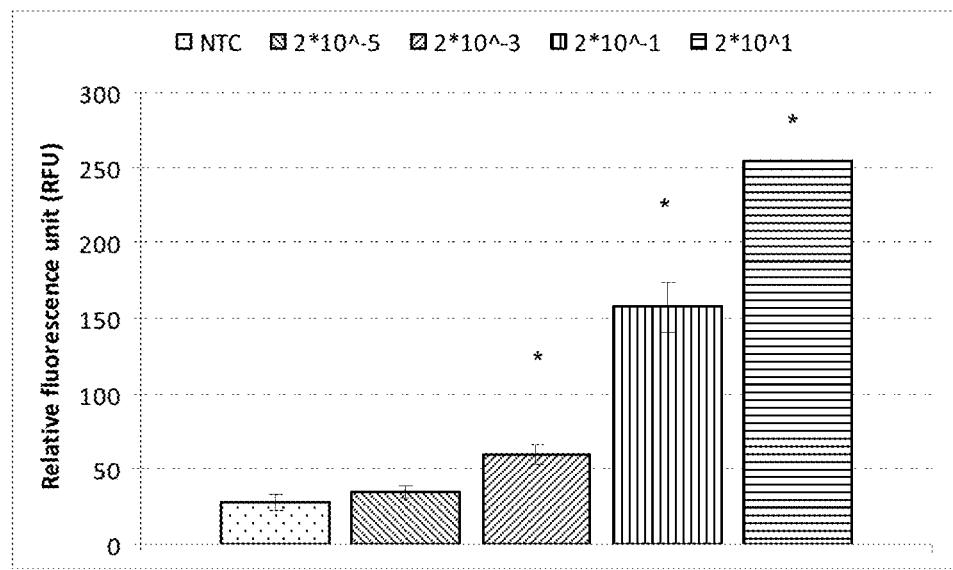
FIG. 13 shows a graph of the fluorescence of mecA DNA template concentrations varied at 0 ng/µL (no-template control (NTC)), $2\times10^{-5}$ ng/µL, $2\times10^{-3}$ ng/µL, $2\times10^{-1}$ ng/µL, and $2\times10^{1}$ ng/µL using the disclosed device in Example 6. It is shown that the mecA target gene can be detected down to a detection limit of $2\times10^{-3}$ ng/µL.

FIG. 13 shows that the disclosed device can detect the mecA target gene down to a detection limit of $2\times10^{-3}$ ng/μL.

The same target gene was detected in a real-time setting using the CFX96 machine obtained from Bio-Rad Laboratories, Inc., CA, USA, as a gold standard comparison. The same primer pair and MB probe were used. The mecA DNA template concentrations were varied at 0 ng/μL (NTC), $2\times10^{-11}$ ng/μL, $2\times10^{-9}$ ng/μL, $2\times10^{-7}$ ng/μL, $2\times10^{-5}$ ng/μL, $2\times10^{-3}$ ng/μL, $2\times10^{-1}$ ng/μL and $2\times10^{1}$ ng/μL. Real-time PCR was performed in triplicates with 25 μL each.

Figure 14:
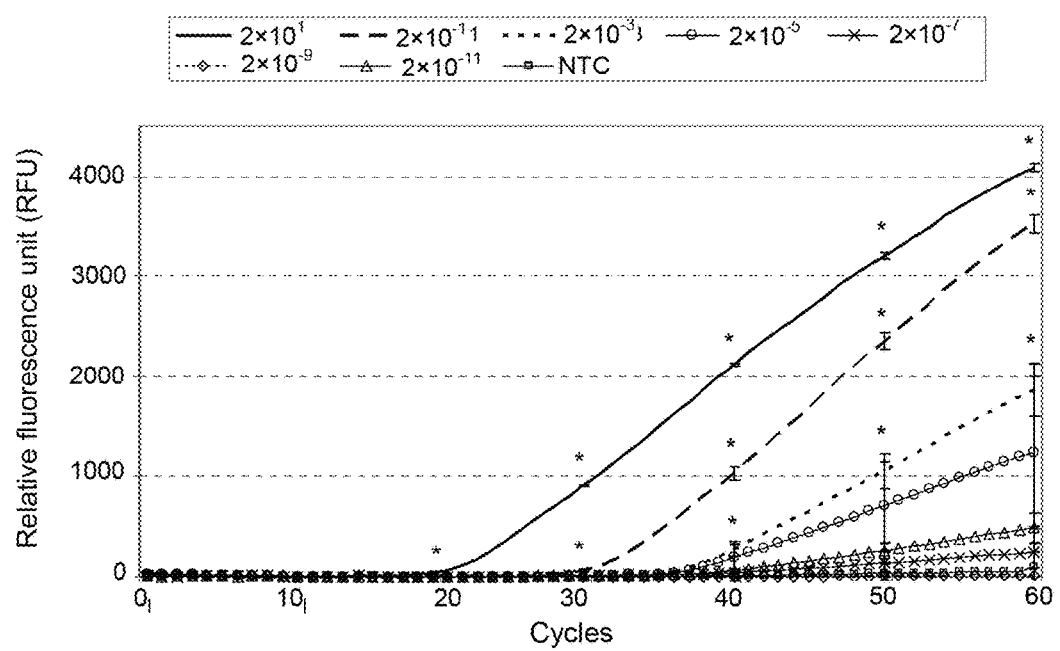
FIG. 14 shows a graph of the fluorescence of mecA DNA template concentrations varied at 0 ng/µL (NTC), $2\times10^{-11}$ ng/µL, $2\times10^{-9}$ ng/µL, $2\times10^{-7}$ ng/µL, $2\times10^{-5}$ ng/µL, $2\times10^{-3}$ ng/µL, $2\times10^{-1}$ ng/µL and $2\times10^{1}$ ng/µL in a real-time PCR assay using the CFX96 machine as a gold standard comparison in Example 6. It is shown that the mecA target gene can be detected down to a detection limit of $2\times10^{-3}$ ng/µL. Hence, the detection sensitivity of the disclosed device is comparable to that of the CFX96 machine.

FIG. 14 shows that the CFX96 machine can detect the mecA target gene down to a detection limit of $2\times10^{-3}$ ng/μL. In FIG. 14, the "*" represents $p\leq0.05$.

Hence, the detection sensitivity of the disclosed device is comparable to that of the CFX96 machine.

---

The invention claimed is:

1. A microfluidic device comprising:
a plurality of wells, each well having an inlet and an outlet, wherein the inlets are in fluid communication with one or more entry channels and the outlets are in fluid communication with one or more exit channels, wherein said outlet is connected to the exit channel via an outlet connecting channel and said inlet is connected to the entry channel via an inlet connecting channel wherein the dimension of the outlet connecting channel is configured such that the surface tension of a liquid comprised in the well prevents the release of the liquid through the outlet connecting channel;
wherein the outlet connecting channel comprises a converging zone, said converging zone having an inclined surface connecting a base of the well with said outlet connecting channel;
wherein a side wall of said converging zone forms an angle (a) with a longitudinal axis through the outlet connecting channel;
wherein the inclined surface of said converging zone forms an angle (b) with the bottom of the outlet connecting channel; and
wherein angle (a) is between about 30° to 60° and (b) is between about 40° to 70°.

2. The device of claim 1, wherein the device comprises a single entry channel and optionally a single exit channel, wherein the single entry channel connects all inlets with each other and the optional single exit channel connects all outlets with each other.

3. The device of claim 1, wherein each well comprises a detection probe, and the detection probe is optionally a lyophilized detection probe.

4. The device of claim 3, wherein the detection probe in each well binds specifically to a different target molecule, and the target molecule is the product of an amplification reaction.

5. The device of claim 1, wherein the plurality of wells is arranged on the device in a radially symmetrical pattern.

6. The device of claim 1, wherein the dimension of the outlet connecting channel is between about 0.05 to 3 mm by between about 0.05 to 3 mm, or between about 0.2 mm by 0.2 mm.

7. The device of claim 1, wherein the volume of each well is independently selected to be between about 1 to 10 μl.

8. The device of claim 1, wherein the plurality of wells is in the range of between about 2 to 100, or 5 to 100, or 5 to 50.

9. The device of claim 1, wherein the entry channel is in fluid communication with any one of the following: a vacuum source connected to a first end of the entry channel or a vacuum source connected to a first end of the entry channel via a liquid trap, a sealant source connected to a second end of the entry channel, a gas source connected to the second end of the entry channel and a source comprising a possible target molecule connected to the second end of the entry channel, and the exit channel is in fluid communication with any one of the following: a vacuum source connected to a first end of the exit channel or a vacuum source connected to a first end of the exit channel via a liquid trap and a sealant source connected to a second end of the exit channel.

10. The device of claim 9, wherein the connection to the sources is controlled by one or more valves which can be controlled separately.

11. The device of claim 1, wherein the material covering or forming the top or top and bottom of the well is made of a transparent material while the remaining device is made of a translucent material.

12. A system comprising:
   a device of claim 1; and
   a detection device arranged above or below the device for detecting a signal emitted by the possible reaction products comprised in the wells during use.

13. The system of claim 12, further comprising one or more of:
   a sealant source connectable to the device to be in fluid communication with the entry channel and/or exit channel,
   a gas source connectable to the device to be in fluid communication with the entry channel,
   a source comprising a possible target molecule connectable to the device to be in fluid communication with the entry channel, and
   a vacuum source connected to the exit and/or entry channel or a vacuum source connected to the exit and/or entry channel via a liquid trap.

14. The system of claim 12, wherein the plurality of wells is arranged to be in thermal communication with a heating element, and the detection device is further capable of emitting a signal for exciting the possible reaction product comprised in the well.

15. A method of detecting at least one target molecule from a liquid sample using the system of claim 12, wherein the method sequentially comprises:
   filling the plurality of wells with the liquid sample by pumping the liquid sample from the source comprising the possible target molecule into the entry channel at a flow rate selected to allow inflow of the liquid sample into the plurality of wells while avoiding release of the liquid into the exit channel,
   removing excess liquid in the entry channel by pulling a vacuum from the vacuum source connected to the entry channel,
   pumping sealant into the entry channel followed by pumping sealant into the exit channel to thereby isolate the liquid sample in each well, and
   detecting a possible signal emitted by a reaction product between the target molecule and the detection probe.

16. The method of claim 15, wherein the plurality of wells are sequentially filled with the liquid sample, and the liquid sample is pumped at a flow rate of between about 10 mL/h to 120 mL/h, or 10 mL/h to 100 mL/h.

17. The method of claim 15, wherein the target molecule is the reaction product of an amplification reaction, preferably an asymmetric polymerase chain reaction (PCR).

18. The method of claim 15, wherein the pumping of sealant into the entry channel is at a flow rate of between about 10 mL/h to 40 mL/h, and the pumping of sealant into the exit channel is at a flow rate of between about 10 mL/h to 80 mL/h.

19. The method of claim 15, wherein the sealant is liquid wax.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Forward excess primer for nuc gene (5'-3')

<400> SEQUENCE: 1
aagcatcaaa ttatagtaag aagac                                25

<210> SEQ ID NO 2
<211> LENGTH: 20
<212> TYPE: DNA
<213> ORGANISM: Artificial Sequence
<220> FEATURE:
<223> OTHER INFORMATION: Reverse limiting primer for nuc gene (5'-3')

<400> SEQUENCE: 2
gccaatgttc taccatagcg                                      20

<210> SEQ ID NO 3
<211> LENGTH: 32
<212> TYPE: DNA
<213> ORGANISM: Artificial Sequence
<220> FEATURE:
<223> OTHER INFORMATION: Molecular beacon probe for nuc gene (5'-3')

<400> SEQUENCE: 3
cgcgcttcta aataaacatc ttgatttgcg cg                        32

<210> SEQ ID NO 4
<211> LENGTH: 21
<212> TYPE: DNA
<213> ORGANISM: Artificial Sequence
<220> FEATURE:
<223> OTHER INFORMATION: Forward excess primer for mecA gene (5'-3')

<400> SEQUENCE: 4
atctgatgat tctattgctt g                                    21

<210> SEQ ID NO 5
<211> LENGTH: 25
<212> TYPE: DNA
<213> ORGANISM: Artificial Sequence
<220> FEATURE:
<223> OTHER INFORMATION: Reverse limiting primer for mecA gene (5'-3')

<400> SEQUENCE: 5
acaacgttac aagatatgaa gtggt                                25

```
<210> SEQ ID NO 6
<211> LENGTH: 32
<212> TYPE: DNA
<213> ORGANISM: Artificial Sequence
<220> FEATURE:
<223> OTHER INFORMATION: Molecular beacon probe for mecA gene (5'-3')

<400> SEQUENCE: 6
cgcgcaaatg gtaatatcga cttaaaagcg cg                                    32

<210> SEQ ID NO 7
<211> LENGTH: 22
<212> TYPE: DNA
<213> ORGANISM: Artificial Sequence
<220> FEATURE:
<223> OTHER INFORMATION: Forward excess primer for blaZ gene (5'-3')

<400> SEQUENCE: 7
gagataaagt aacaaatcca gt                                               22

<210> SEQ ID NO 8
<211> LENGTH: 20
<212> TYPE: DNA
<213> ORGANISM: Artificial Sequence
<220> FEATURE:
<223> OTHER INFORMATION: Reverse limiting primer for blaZ gene (5'-3')

<400> SEQUENCE: 8
ccgaaagcag caggtgttga                                                  20

<210> SEQ ID NO 9
<211> LENGTH: 36
<212> TYPE: DNA
<213> ORGANISM: Artificial Sequence
<220> FEATURE:
<223> OTHER INFORMATION: Molecular beacon probe for blaZ gene (5'-3')

<400> SEQUENCE: 9
cgcgcttttt gctctttggt gaatagtaat tgcgcg                                36
```